(12) United States Patent
Kim et al.

(10) Patent No.: US 11,008,622 B2
(45) Date of Patent: May 18, 2021

(54) BIOMARKER FOR PREDICTING SENSITIVITY TO EGFR-TARGETING AGENT, AND USE THEREOF

(71) Applicant: THE ASAN FOUNDATION, Seoul (KR)

(72) Inventors: Tae Won Kim, Seoul (KR); Dong Hoon Jin, Seoul (KR); Seung Woo Hong, Seoul (KR); Jai Hee Moon, Seoul (KR); Jae Sik Shin, Seoul (KR); Seung Mi Kim, Seoul (KR); Dae Hee Lee, Seoul (KR); Eun Young Lee, Seoul (KR); Seul Lee, Seoul (KR); Yong Sang Hong, Seoul (KR)

(73) Assignee: Wellmarker Bio Co., Ltd., Seoul (KR)

( * ) Notice: Subject to any disclaimer, the term of this patent is extended or adjusted under 35 U.S.C. 154(b) by 636 days.

(21) Appl. No.: 15/329,942

(22) PCT Filed: Jul. 29, 2015

(86) PCT No.: PCT/KR2015/007964
§ 371 (c)(1),
(2) Date: Jan. 27, 2017

(87) PCT Pub. No.: WO2016/018087
PCT Pub. Date: Feb. 4, 2016

(65) Prior Publication Data
US 2019/0127802 A1  May 2, 2019

(30) Foreign Application Priority Data

Jul. 29, 2014  (KR) ........................ 10-2014-0096716

(51) Int. Cl.
*C12Q 1/6886* (2018.01)
*C12Q 1/68* (2018.01)
*A61P 43/00* (2006.01)
*A61P 35/00* (2006.01)

(52) U.S. Cl.
CPC ............ *C12Q 1/6886* (2013.01); *A61P 35/00* (2018.01); *A61P 43/00* (2018.01); *C12Q 1/68* (2013.01); *C12Q 2600/106* (2013.01); *C12Q 2600/118* (2013.01); *C12Q 2600/156* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2012/0089541 A1* | 4/2012 | Patel ................ G01N 33/57423 705/500 |
| 2012/0107304 A1* | 5/2012 | Solca ..................... A61K 31/00 424/133.1 |

OTHER PUBLICATIONS

Weinstein-Oppenheimer, et al., "The Raf signal transuction cascade as a target for chemotherapeutic intervention in growth factor-responsive tumors", Pharmacology & Therapeutics 88, 2000, pp. 229-279.

* cited by examiner

*Primary Examiner* — Katherine D Salmon
(74) *Attorney, Agent, or Firm* — Stoel Rives LLP; Kelly A. Echols

(57) ABSTRACT

The present disclosure relates to a new biomarker for predicting susceptibility to an EGFR-targeted agent and a use thereof, and more particularly, provides a biomarker for predicting susceptibility to an EGFR (Epidermal Growth Factor Receptor)-targeted agent, comprising a RON (Recepteur d'Origine Nantais) gene; a composition for predicting susceptibility to the EGFR-targeted agent, comprising an agent which measures a gene expression level of the biomarker; or an expression or activity level of a protein thereof; a composition for enhancing the susceptibility to the EGFR-targeted agent, comprising an inhibitor of the expression of the gene or the expression or activity of the protein of the gene as active ingredients; a kit for predicting the susceptibility to the EGFR-targeted agent, comprising the composition; and a method for predicting the susceptibility to the EGFR-targeted agent. According to the present disclosure, since an effect of predicting the susceptibility to the EGFR-targeted agent is excellent in a colon cancer, the present disclosure may be useful in the treatment of the colon cancer.

3 Claims, 20 Drawing Sheets
Specification includes a Sequence Listing.

BIOMARKER FOR PREDICTING SENSITIVITY TO EGFR-TARGETING AGENT, AND USE THEREOF

RELATED APPLICATIONS

This application is a United States National Phase entry of International Application No. PCT/KR2015/007964 filed Jul. 29, 2015, which claims the benefit of Korean Patent Application No. 10-2014-0096716 filed Jul. 29, 2014. The entire contents of both of the foregoing applications are hereby incorporated by reference herein.

TECHNICAL FIELD

The present disclosure is achieved by Project No. 1420030 under the support of the Ministry of Health of Korea and a research management specialized organization of the project is Research Supporting Program for Regional Cancer Center, a research program name is "National R&D Program for Cancer Control", a research project name is "Development of New Therapy for Overcoming Centuximab Resistance in Colon Cancer Patient and Development of Biomarker", a control organization is Asan Medical Center, and a research period is May 1, 2014 to Apr. 30, 2017.

The present disclosure is achieved by Project No. HI06C0868 under the support of the Ministry of Health of Korea and the research management specialized organization of the report is Korea Health Industry Development Institute, the research program name is "Leading Characterization Research Program", the research project name is "Development of Creative Anticancer Drug Targeting Receptor Tyrosine Kinase (RTK)", the control organization is Leading Cancer Research Business Group of Asan Medical Center, and the research period is Dec. 1, 2011 to Nov. 30, 2016.

The present disclosure relates to a new biomarker for predicting susceptibility to an EGFR-targeted agent and a use thereof.

BACKGROUND

Generally, in an anticancer therapy, a biological response when administering an anticancer agent significantly depends on susceptibility to the anticancer agent of cancer cells targeted to the anticancer agent. The susceptibility of the cancer cell to the anticancer agent significantly varies for each cancer cell. The difference in susceptibility is caused due to a quantitative or qualitative difference of a target molecule of the cancer agent or a factor associated therewith or acquisition of drug-resistance. Based on the background, when a targeted cancer cell exhibits the susceptibility to the drug, if a genetic change of the cancer cell specifically exhibited may be verified, determination of an effect of the drug, establishment of the therapy, selection of a new therapy and the like are valid, and as a result, it is greatly beneficial. Further, in a cancer tissue obtained by a bio tissue piece, and the like prior to therapy, the cancer cell is separated and drug processing is performed according to a general method, and as a result, when whether the cancel cell is sensitive to the drug is measured by the change, whether the therapy by the drug is valid may be predicted, it is very useful clinically.

In general, it was known that mutation of a KRAS, NRAS, or BRAF gene makes protein having a signaling characteristic deformed from the cancer cell and the mutation is associated with an unsuccessful result in a cancer therapy using a therapeutic antibody targeting an epidermal growth factor receptor, for example, cetuximab or panitumumab (Amado, Wolf et al, 2008; Karapetis, Khambata-Ford et al, 2008; Di Nicolantonio, Martini et al, 2008; Loupakis, Ruzzo et al, 2009; Lievre, 1Bachet et al, 2006).

However, even in the case of a cancer patient having not mutation but a KRAS, NRAS, or BRAF wild type genotype, there are many cases in which an anticancer effect of a target anticancer agent such as cetuximab, or the like is less.

Cetuximab as a recombination anti-EGFR human/mouse chimeric monoclonal antibody (MoAb) was known to sensitize the cancer cell to antibody-dependent cell toxicity, and chemotherapy and radiotherapy (Graham J, et al., Nat Rev Drug Discov. July 2004; 3(7):549-50; Kimura H. et al., Cancer Sci. August 2007; 98(8):1275-80; Kurai J, et al., Clin Cancer Res. Mar. 1, 2007; 13(5):1552-61; Dittmann K. et al., RadiotherOncol, August 2005; 76(2):157-61). Due to the advantage, a clinical advantage using cetuximab as a single therapy or a concurrent therapy of chemotherapy and/or radiotherapy has been proved in head cancer and cervical cancer and metastatic colon cancer (Marshall J, et al., Cancer. Sep. 15, 2006; 107(6):1207-18).

Meanwhile, Recepteur d'Origine Nantais (RON) as a protein receptor that belongs to c-MET series is a receptor of macrophage-stimulating protein (MSP) secreted from liver and controlling an operation of macrophagocyte (Zhou Y Q, He C, Chen Y Q, Wang D, Wang M H: Altered expression of the RON receptor tyrosine kinase in primary human colorectal adenocarcinomas, generation of different splicing RON variants and their oncogenic potential, Oncogene 2003, 22(2):186-197). Expression of RON is abnormally controlled in breast cancer and colorectal cancer and in particular, is closed related with metastasis of colorectal cancer. For example, as it is reported that a single clone antibody IMC-41A10 bonded to RON inhibits cell metastasis and cancer formation, a RON inhibitor will be able to exhibit an excellent effect in anti-cancer and cancer metastasis.

That is, an anti-cancer drug exhibits a large difference among individuals in terms of resistance and toxicity and since the anti-cancer drug exhibits resistance over the half number even in the same patient, and as a result, selection using an appropriate therapeutic responsiveness marker may bring about a remarkable advance in anti-cancer drug therapy. Therefore, a research into therapy responsiveness of individual anti-cancer drugs depending on a specific gene has been continuously actively progressed in recent years.

However, there is no notable accomplishments due to a complex operation of a bio response related element to a specific drug, diversity of medicines and administration schemes, and a difficulty in securing enormous samples.

SUMMARY

The present inventors have made intensive efforts to develop the method for predicting the susceptibility to the EGFR-targeted agent as the anticancer agent in the colon cancer by analyzing an activity level of the RON gene and/or the protein as the biomarker for predicting the susceptibility in the colon cancer to cetuximab which is one of EGFR-targeted agents. As results, the present inventors has verified that the cell death degree is different by the drug susceptibility to cetuximab as the EGFR-targeted agent by having an effect on the Adam11, Adam32, FZD4, GPER, and GPR101 genes which are EGFR-transactivation-related genes according to the activity level of the RON gene and/or the protein in the colon cancer, thereby completing the present disclosure.

Accordingly, it is an object of this invention to provide a biomarker for predicting susceptibility to an EGFR-targeted agent.

It is another object of this invention to provide a composition for predicting susceptibility to an EGFR-targeted agent.

It is yet another object of this invention to provide a composition for predicting susceptibility to an EGFR-targeted agent.

It is still another object of this invention to provide a kit for predicting susceptibility to an EGFR-targeted agent.

It is still yet another object of this invention to provide a susceptibility enhancer to an EGFR-targeted agent.

It is still yet another object of this invention to provide a method for predicting susceptibility to an EGFR-targeted agent.

It is still yet another object of this invention to provide a pharmaceutical composition for preventing or treating cancer, comprising the susceptibility enhancer to the EGFR-targeted agent and the EGFR-targeted agent as active ingredients.

It is still yet another object of this invention to provide a method for enhancing susceptibility to the EGFR-targeted agent, comprising administering the susceptibility enhancer to the EGFR-targeted agent and the EGFR-targeted agent to a subject.

According to the embodiment of the present disclosure, when the biomarker for predicting the susceptibility to the EGFR-targeted agent is used, the susceptibility of an individual patient may be accurately determined before treatment initiation, and thus, it is possible to select an anticancer agent having a high treatment effect. Further, since the use of the anticancer agent without obtaining the effect is avoided, it is possible to avoid unnecessary side effects.

DETAILED DESCRIPTION

Figure 1A:
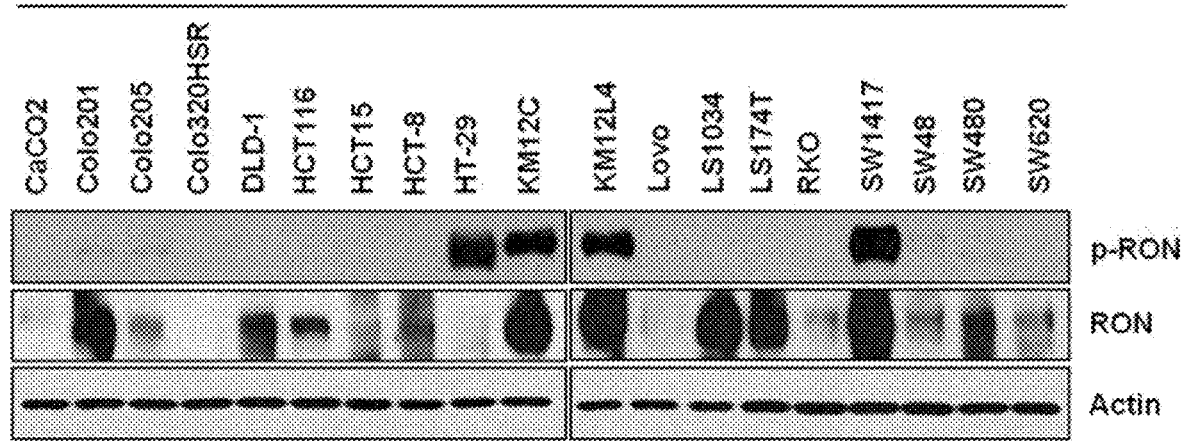
FIG. 1A illustrates presence or absence of activation of RON proteins in a human colon cancer cell line.

Hereinafter, the present disclosure will be described in more detail.

In one aspect of the present invention, there is provided a biomarker or a biomarker composition for predicting susceptibility to an epidermal growth factor receptor (EGFR)-targeted agent including a recepteur d' origine nantais (RON, NM 002447.1) gene.

The largest feature of the present disclosure is to predict susceptibility to the EGFR-targeted agent using activation of the RON gene and an activated protein which is a product thereof as a biomarker.

The biomarker of the present disclosure may be an indicator of susceptibility to an anticancer agent which is the EGFR-targeted agent and may be used in treatment of generation, development, and/or metastasis of the cancer due to excellent accuracy and reliability as a sensitive marker to the anticancer agent.

The term "susceptibility" used in this specification means whether to have an effect on a specific drug for the cancer of a subject patient.

The term "susceptibility" used while mentioning the susceptibility in this specification means that an effect on the drug is acted by susceptibly reacting with the corresponding drug and is mixed with the susceptibility in this specification.

The term "resistance" used while mentioning the susceptibility in this specification means that the effect on the drug is not acted without susceptibly reacting with the corresponding drug.

For example, the specific drugs are mainly anticancer agents, and the anticancer agents have the effect on the cancer or not depending on the type of cancer. Further, in spite of a kind of cancer that is recognized as valid, it is known that there are a case with the effect and a case without the effect according to a target subject patient. Whether the anticancer agent has an effect on the cancer of the target patient is referred to as susceptibility to the anticancer agent. Accordingly, according to the present disclosure, if patients (responders) that may expect the effect before treatment initiation and patients (non-responders) which may not expect the effect can be predicted, chemotherapy with high effectiveness and safety may be implemented.

The term "prediction" used in this specification is used to indicate possibility of advantageously or disadvantageously responding to a drug or a drug set of the target patient. In an embodiment, the prediction relates to the degree of the response. For example, the prediction relates to presence or absence of survival without cancer recurrence and/or probability thereof after treatment of the patient, for example, treatment of a specific therapeutic agent and/or surgical removal of a primary tumor and/or chemotherapy for a predetermined period. The prediction of the present disclosure may be clinically used to determine the treatment by selecting the most appropriate treatment method for the colon cancer patient. The prediction of the present disclosure is a useful tool for predicting whether the patient advantageously responds to a therapeutic treatment, for example, a given therapeutic treatment, such as administration, surgical intervention, chemotherapy of a given therapeutic agent or a combination thereof or whether long-term survival of the patient after the therapeutic treatment is possible.

According to a preferred embodiment of the present disclosure, the biomarker of the present disclosure further includes one or more genes selected from the group consisting of KRAS (V-Ki-ras2 Kirsten rat sarcoma viral oncogene homolog, Gene Bank accession No. NM_033360.2), NRAS (neuroblastoma RAS viral (v-ras) oncogene homolog, Gene Bank accession No. NP_002515.1), BRAF (v-raf murine sarcoma viral oncogene homolog B, Gene Bank accession No. NP_004324.2), EGFR (Epidermal Growth Factor Receptor, Gene Bank accession No. U48722.1), Adam11 (ADAM metallopeptidase domain 11, Gene Bank accession No. NM_002390.4), Adam32 (ADAM metallopeptidase domain 32, Gene Bank accession No. NM_145004.5), FZD4 (Frizzled family receptor 4, Gene Bank accession No. NM_012193.2), GPER (G protein-coupled estrogen receptor 1, NM_001505.2), and GPR101 (G protein-coupled receptor 101, Gene Bank accession No. NM_054021.1) genes.

Further, according to a preferred embodiment of the present disclosure, when the KRAS (V-Ki-ras2 Kirsten rat sarcoma viral oncogene homolog, NM_033360.2), NRAS (neuroblastoma RAS viral (v-ras) oncogene homolog, NP_002515.1), or BRAF (v-raf murine sarcoma viral oncogene homolog B, NP_004324.2) gene is a wild type, the biomarker of the present disclosure predicts the susceptibility to the EGFR-targeted agent and may be applied to a case where cancer cells with KRAS, NRAS, or BRAF mutation do not achieve a desired effect.

That is, in the present disclosure, the biomarker verifies whether the genes in the cells are present as the wild type by using the RON, KRAS, NRAS, or BRAF gene and targeting an target having cancer cells or cancer with the KRAS, NRAS, or BRAF wild-type gene. When the expression level of the RON gene or the protein expression thereof or the activity level is low as compared with a normal level (alternatively, the expression level of the wild-type gene/or the protein), the biomarker determines that there is the susceptibility to the EGFR-targeted agent. When the expression level of the RON gene or the protein expression thereof or the activity level is high as compared with a normal level, the biomarker determines that there is the resistance to the EGFR-targeted agent.

Further, the Adam11 (ADAM metallopeptidase domain 11, NM_002390.4), Adam32 (ADAM metallopeptidase domain 32, NM_145004.5), FZD4 (Frizzled family receptor 4, NM_012193.2), GPER (G protein-coupled estrogen receptor 1, NM_001505.2), GPR101 (G protein-coupled receptor 101, NM_054021.1) genes are EGFR transcriptional activity-related genes and may be included as the biomarker that predicts the susceptibility to the EGFR-targeted agent by the RON gene because the expression thereof is induced according to the activity of the RON gene as the biomarker of the present disclosure and the active protein as the product thereof.

Further, the EGFR (Epidermal Growth Factor Receptor, Gene Bank accession number U48722.1) gene may be included as the biomarker that predicts the susceptibility to the EGFR-targeted agent by the RON gene because the activation is induced or increased according to the activity of the RON gene as the biomarker of the present disclosure and the active protein as the product thereof.

In another aspect of the present invention, there is provided a composition for predicting the susceptibility to the EGFR-targeted agent including an agent that measures an expression level of RON (Recepteur d'Origine Nantais, Gene Bank accession number NM_002447.1) gene or an expression or activity level of the protein thereof.

According to another embodiment of the present disclosure, the composition of the present disclosure further includes an agent that measures an expression level of one or more genes selected from the group consisting of KRAS (V-Ki-ras2 Kirsten rat sarcoma viral oncogene homolog, Gene Bank accession No. NM_033360.2), NRAS (neuroblastoma RAS viral (v-ras) oncogene homolog, Gene Bank accession No. NP_002515.1), BRAF (v-raf murine sarcoma viral oncogene homolog B, Gene Bank accession No. NP_004324.2), EGFR (Epidermal Growth Factor Receptor, Gene Bank accession No. U48722.1), Adam11 (ADAM metallopeptidase domain 11, Gene Bank accession No. NM_002390.4), Adam32 (ADAM metallopeptidase domain 32, Gene Bank accession No. NM_145004.5), FZD4 (Frizzled family receptor 4, Gene Bank accession No. NM_012193.2), GPER (G protein-coupled estrogen receptor 1, NM_001505.2), and GPR101 (G protein-coupled receptor 101, Gene Bank accession No. NM_054021.1) genes; or an expression or activity level of the protein of the genes.

Further, according to a preferred embodiment of the present disclosure, when the KRAS (V-Ki-ras2 Kirsten rat sarcoma viral oncogene homolog, NM_033360.2), NRAS (neuroblastoma RAS viral (v-ras) oncogene homolog, NP_002515.1), or BRAF (v-raf murine sarcoma viral oncogene homolog B, NP_004324.2) gene is a wild type, the composition of the present disclosure predicts the susceptibility to the EGFR-targeted agent and may be applied to a case where cancer cells with KRAS, NRAS, or BRAF mutation do not achieve a desired effect.

Further, according to a preferred embodiment of the present disclosure, the EGFR-targeted agent is a therapeutic agent for one or more selected from the group consisting of adrenocorticotropic hormone (ACTH) produced tumors, acute lymphocytic or lymphoblastic leukemia, acute or chronic lymphocytic leukemia, acute non-lymphocytic leukemia, bladder cancer, brain tumors, breast cancer, cervix cancer, chronic myelogenous leukemia, lymphomas, endometriosis, esophagus cancer, bladder cancer, Ewing's sarcoma, tongue cancer, Hopkins lymphoma, Capo sheath sarcoma, kidney cancer, liver cancer, lung cancer, mesothelioma, multiple myeloma, neuroblastoma, non-hopkin lymphoma, osteosarcoma, ovarian cancer, lobular carcinoma, prostate cancer, pancreatic cancer, colon cancer, penis cancer, retinoblastoma, skin cancer, stomach cancer, thyroid cancer, uterine cancer, testicular cancer, wilms tumor, and trophoblastoma. Further, according to a more preferred embodiment of the present disclosure, the EGFR-targeted agent is a therapeutic agent for one or more selected from the group consisting of adrenocorticotropic hormone (ACTH) produced tumors, acute lymphocytic or lymphoblastic leukemia, acute or chronic lymphocytic leukemia, acute non-lymphocytic leukemia, bladder cancer, brain tumors, breast cancer, cervix cancer, chronic myelogenous leukemia, lymphomas, endometriosis, esophagus cancer, bladder cancer, Ewing's sarcoma, tongue cancer, Hopkins lymphoma, Capo sheath sarcoma, kidney cancer, liver cancer, lung cancer, mesothelioma, multiple myeloma, neuroblastoma, non-hopkin lymphoma, osteosarcoma, ovarian cancer, lobular carcinoma, prostate cancer, pancreatic cancer, colon cancer, penis cancer, retinoblastoma, skin cancer, stomach cancer, thyroid cancer, uterine cancer, testicular cancer, Wilms tumor, and trophoblastoma. According to a still more preferred embodiment of the present disclosure, the EGFR-targeted agent is a therapeutic agent for colon cancer.

The term "colon cancer" used in this specification means a common name of rectal cancer, colorectal cancer, and anal cancer.

Further, the EGFR-targeted agent of the present disclosure means an anticancer agent and any EGFR-targeted agent that has an anticancer effect may be applied. Preferably, the EGFR-targeted agent is one or more selected from the group consisting of cetuximab, gefitinib, erlotinib, panitumumab, PKI-166, EKB-569, HKI-272 (WAY-177820), icotinib, brigatinib, afatinib, lapatinib, canertinib, AEE788, XL647, and Zactima. The EGFR-targeted agent is more preferably cetuximab, gefitinib, erlotinib, or panitumumab, and most preferably cetuximab.

Unless stated otherwise in this specification, the expression "measuring the expression level of the gene; or the expression or activity level of the protein of the gene" used in this specification means detecting a target to be detected in the corresponding sample.

In the present disclosure, the target to be detected is mRNA and/or protein of the corresponding gene in the sample. That is, whether the gene is expressed or not may be verified by detecting RNA as a transcription product of the gene or protein (preferably, the active form) as a gene product.

The detecting of the RNA or the protein may be generally implemented by extracting the RNA or the protein from the sample to detect the RNA or the protein from the extractant. The detecting of the RNA or the protein may be measured by an immunological analytical method, a hybridization reaction, and an amplification reaction, but is not limited thereto and may be easily implemented by using various techniques known in the art.

Further, according to a preferred embodiment of the present disclosure, the agent that measures the gene expression level includes antisense oligonucleotide, a primer pair, or a probe which is specifically bound to the mRNA of the gene.

The agent that measures the expression of the mRNA is selected from the group consisting of antisense oligonucleotide, a primer pair, a probe, and a combination thereof that are specific to the gene. That is, the detecting of nucleic acid may be performed by an amplification reaction using one or more oligonucleotide primers which are hybridized to a nucleic acid molecule encoding the gene or a complementary material of the nucleic acid molecule.

For example, the detecting of the mRNA using the primer may be performed by verifying whether the gene is amplified by a known method in the art after amplifying a gene sequence by using the amplification method such as PCR.

Further, according to a preferred embodiment of the present disclosure, the agent that measures the expression or activity level of the protein includes an antibody, a peptide, or a nucleotide which is specifically bound to the protein.

The agent that measures the expression or activity level of the protein means an antibody which is specifically bound to the protein and includes a polyclonal antibody, a monoclonal antibody, a recombinant antibody, and a combination thereof.

The antibody includes all of not only the polyclonal antibody, the monoclonal antibody, the recombinant antibody, and a complete form having two light chains with the full length and two heavy chains with the full length, but also functional fragments of the antibody molecules, for example, Fab, F(ab'), F(ab')2, and Fv. The antibodies may be easily prepared by using a well-known technique in the art and antibodies which are prepared and commercially sold may be used.

The composition of the present disclosure may further include labels which may quantitatively or qualitatively measure formation of an antigen-antibody complex, general tools used in the immunological analysis, reagents, and the like as well as the agent for measuring whether the above-described gene is expressed or not.

The labels which may quantitatively or qualitatively measure the formation of the antigen-antibody complex include enzymes, fluorescent substances, ligands, luminescent substances, microparticles, redox molecules, radioactive isotopes, and the like, and are not necessarily limited thereto.

The enzymes usable as the detection label include β-glucuronidase, β-D-glucosidase, β-D-galactosidase, urease, peroxidase, alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, β-lactamase, and the like, and are not limited thereto. The fluorescent substances include fluorescein, isothiocyanate, rhodamine, phycoerythrin, phycocyanin, allophycocyanin, o-phthaldehyde, fluorescamine, and the like, and are not limited thereto. The ligands include biotin derivatives and the like, and are not limited thereto. The luminescent substances include acridinium ester, luciferin, luciferase, and the like, and are not limited thereto. The microparticles include colloidal gold, colored latex, and the like, and are not limited thereto. The redox molecules include ferrocene, ruthenium complex compounds, viologen, quinone, Ti ions, Cs ions, diimide, 1,4-benzoquinone, hydroquinone, $K_4W(CN)^8$, $[Os(bpy)_3]^{2+}$, $[RU(bpy)_3]^{2+}$, $[MO(CN)_8]^{4-}$, and the like, and are not limited thereto. The radioactive isotopes include $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, and the like, and are not limited thereto.

An example of the tool or the reagent includes suitable carriers, solubilizing agents, detergents, buffering agents, stabilizers, and the like, but is not limited thereto. When the marker is the enzyme, a substance and a quencher which may measure the enzyme activity may be included. The carriers include a soluble carrier, and an insoluble carrier. An example of the soluble carrier includes a buffer solution that is physiologically acceptable and known in the art, for example, PBS, and an example of the insoluble carrier may include polystyrene, polyethylene, polypropylene, polyester, polyacrylonitrile, fluororesin, cross-linked dextran, polysaccharide, and other papers, glass, metal, agarose, and a combination thereof.

Since the composition of the present disclosure uses the aforementioned biomarker, the disclosure of the duplicated contents is omitted for avoiding excessive complexity of this specification.

In yet another aspect of the present invention, there is provided a kit for predicting the susceptibility to the EGFR-targeted agent including the composition.

The kit may include a tool, a reagent, and the like which are generally used in the art for immunological analysis as well as the agent which measures the expression of the gene; or the expression or activity level of the protein thereof.

An example of the tool or the reagent includes suitable carriers, markers capable of generating a detectable signal, chromophores, solubilizing agents, detergents, buffering agents, stabilizers, and the like, but is not limited thereto. When the marker is the enzyme, a substance and a quencher which may measure the enzyme activity may be included. The carriers include a soluble carrier, and an insoluble carrier. An example of the soluble carrier includes a buffer solution that is physiologically acceptable and known in the art, for example, PBS, and an example of the insoluble carrier may include polystyrene, polyethylene, polypropylene, polyester, polyacrylonitrile, fluororesin, cross-linked dextran, polysaccharide, polymers such as magnetic particles plating a metal on the latex, and other papers, glass, metal, agarose, and a combination thereof.

Since the kit of the present disclosure uses the aforementioned biomarker and composition as the configuration, the disclosure of the duplicated contents is omitted for avoiding excessive complexity of this specification.

In still another aspect of the present invention, there is provided a susceptibility enhancer or a composition for enhancing susceptibility to an epidermal growth factor receptor (EGFR)-targeted agent for a subject, including an inhibitor of expression of an RON (Recepteur d'Origine Nantais, NM_002447.1) gene; or expression or activity of the protein of the gene as an active ingredient.

According to a preferred embodiment of the present disclosure, when the KRAS (V-Ki-ras2 Kirsten rat sarcoma viral oncogene homolog, NM_033360.2), NRAS (neuroblastoma RAS viral (v-ras) oncogene homolog, NP_002515.1), or BRAF (v-raf murine sarcoma viral oncogene homolog B, NP_004324.2) gene is a wild type, the target predicts the susceptibility to the EGFR-targeted agent and may be applied to a case where cancer cells with KRAS, NRAS, or BRAF mutation do not achieve a desired effect.

According to the present disclosure, in cancer cells with a KRAS, NRAS, or BRAF wild-type gene in which activity of the RON gene and an active protein as a product thereof are expressed, a result exhibits that a death rate of the cancer cells by cetuximab is significantly decreased as compared with anticancer cells in which the activity of the RON gene and the active protein are not expressed.

Further, in the present disclosure, in the cancer cells with a KRAS, NRAS, or BRAF wild-type gene in which the activity of the RON gene and the active protein as a product thereof are expressed, when the expression of the RON gene; or the expression or activity of the protein is inhibited, a result exhibits that a death rate of the cancer cells by cetuximab is significantly increased.

Accordingly, this indicates that the susceptibility of the cancer cells to cetuximab is enhanced by the presence of the KRAS, NRAS, or BRAF wild-type (normal) gene (normal expression and function of the normal gene); and the expression inhibition of the RON gene, and the present disclosure provides an excellent effect of enhancing the susceptibility of the target to the EGFR-targeted agent based thereon.

The susceptibility enhancer or the composition for enhancing of the present disclosure may additionally include a carrier which is pharmaceutically acceptable. The pharmaceutically acceptable carrier which may be used in the present disclosure may be used by selecting general excipients, disintegrants, binders, lubricants, and other additives, for example, stabilizers, relaxant, emulsifiers, and the like. For example, as the excipients, microcrystalline cellulose, lactose, low-substituted hydroxypropyl cellulose, and the like may be used, and as the disintegrants, sodium starch glycolate, anhydrous dibasic calcium phosphate, and the like may be used. As the binders, polyvinylpyrrolidone, low-substituted hydroxypropyl cellulose, and the like may be used, and the lubricants may be selected and used from magnesium stearate, silicon dioxide, talc, and the like.

In the present disclosure, the presence of the KRAS, NRAS, or BRAF wild-type gene and the expression inhibition of the RON gene reduce the growth of the cancer cells in the treatment of the EGFR-targeted agent.

The expression of the RON gene is inhibited by one or more selected from the group consisting of small interference RNA (siRNA), short hairpin RNA (shRNA), microRNA (miRNA), ribozyme, DNAzyme, peptide nucleic acids (PNAs), antisense oligonucleotide, antibodies, aptamers, natural extracts, and chemical substances that are specifically bound to mRNA of the RON gene.

The expression of the RON gene is inhibited by more preferably antisense oligonucleotide, aptamers, siRNA, shRNA, or miRNA, and most preferably siRNA or antisense oligonucleotide.

The term "siRNA" used in this specification means a small RNA fragment with a size of 21 to 25 nucleotides generated when a double-stranded RNA is cleaved by a dicer and inhibits the expression by specifically bound to mRNA having a complementary sequence. On the purpose of the present disclosure, the term "siRNA" means inhibiting the expression of the gene by specifically bound to RON mRNA. The siRNA may be chemically or enzymatically synthesized. A preparation method of the siRNA is not particularly limited and may use a known method in the art.

According to the preferred embodiment of the present disclosure, the siRNA includes a nucleotide sequence of SEQ ID NO: 13.

The term "antisense oligonucleotide" used in this specification is a nucleotide sequence that inhibits the expression by complementarily bound to the miRNA and is not limited thereto, but includes antisense RNA, antisense DNA, and antagonist mRNA.

Since the susceptibility to the EGFR-targeted agent is enhanced by using the expression level of the aforementioned biomarker in the method of the present disclosure, the disclosure of the duplicated contents is omitted for avoiding excessive complexity of this specification.

In still yet another aspect of the present invention, there is provided a pharmaceutical composition for preventing or treating diseases related with dysregulation of an EGFR signaling pathway, including a susceptibility enhancer to the aforementioned EGFR-targeted agent and the EGFR-targeted agent as the active ingredients.

In the present disclosure, the diseases related with the dysregulation of the EGFR signaling pathway are cancer, atherosclerosis, pulmonary fibrosis, renal fibrosis and regeneration, liver disease, allergic disease, inflammatory disease, autoimmune disorder, cerebrovascular disease, cardiovascular disease, or symptoms associated with organ transplantation, and preferably cancer.

That is, the inhibitor of the expression of the RON (Recepteur d'Origine Nantais, NM_002447.1) gene as the susceptibility enhancer to the EGFR-targeted agent of the present disclosure; or the expression or activity of the protein of the gene increases the susceptibility to the anticancer and increases the anticancer effects of the anticancer agents when being administrated together with the anticancer agents to more facilitate the treatment of the cancer.

The "cancer" which is the disease to be improved, prevented, or treated by the composition of the present disclosure means a common name of diseases caused by cells having an aggressive characteristic in which the cells are divided and grown regardless of a normal growth limit, an invasive characteristic in which the cells are invaded to the ambient tissue, and a metastatic characteristic in which the cells spread to other parts of the body. In this specification, the cancer is used as the same meaning as malignant tumor.

The cancer to which the composition of the present disclosure is applied includes breast cancer, lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, small intestine cancer, endocrine cancer, thyroid cancer, parathyroid cancer, adrenal cancer, soft tissue tumor, urethral cancer, prostate cancer, bronchogenic cancer, bone marrow tumor, and the like, but is not limited thereto.

Preferably, the composition of the present disclosure may be applied to prevent or treat the colon cancer.

The term "prevention" in this specification means that it has been not diagnosed that the diseases or the disorders are preserved, but generation of the diseases or the disorders is suppressed in animals which are susceptible to the diseases or the disorders. The term "treatment" in this specification means (i) suppression of development of the diseases or the disorders; (ii) reduction of the diseases or the disorders; and (iii) removal of the diseases or the disorders.

Further, the composition of the present disclosure may further include a pharmaceutically acceptable carrier.

The pharmaceutically acceptable carrier included in the pharmaceutical composition of the present disclosure is generally used in the preparation, and includes lactose, dextrose, sucrose, sorbitol, mannitol, starches, gum acacia, calcium phosphate, alginate, gelatin, calcium silicate, microcrystalline cellulose, polyvinylpyrrolidone, cellulose, water, syrup, methyl cellulose, methylhydroxy benzoate, propyl hydroxybenzoate, talc, magnesium stearate, mineral oils, and the like, but is not limited thereto. The pharmaceutical composition of the present disclosure may additionally include a lubricant, a wetting agent, a sweetener, a flavoring agent, an emulsifier, a suspension, a preservative, and the like other than the components. The suitable pharmaceutically acceptable carrier and agent are disclosed in detail in Remington's Pharmaceutical Sciences (19th ed., 1995).

A suitable dosage of the pharmaceutical composition of the present disclosure may be prescribed by various methods according to factors, such as formulation methods, administration methods, patient's age, body weight, sex, morbidity, food, time of administration, a route of administration, an excretion rate, and response susceptibility.

Meanwhile, the dosage of the pharmaceutical composition of the present disclosure is preferably 0.001 to 1000 mg/kg (weight) per day.

The pharmaceutical composition of the present disclosure may be orally or parenterally administrated, and in the case of the parental administration, the pharmaceutical composition may be administrated by Intravenous injection, subcutaneous injection, intramuscular injection, intraperitoneal injection, dermal administration, and the like. It is preferred that the administration route is determined according to a kind of disease to which the pharmaceutical composition of the present disclosure is applied.

The concentration of the corresponding gene or the expression inhibitor of the protein thereof in the enhancer as the active ingredient included in the composition of the present disclosure is determined by considering a therapeutic purpose, a patient's condition, a required period, the severity of the disease, and the like and is not limited to a concentration in a predetermined range.

The pharmaceutical composition of the present disclosure is formulated by using the pharmaceutically acceptable carrier and/or the excipient according to a method which may be easily implemented by those skilled in the art to be prepared in a unit capacity form or inserted into a large-capacity container to be prepared. In this case, the formulation may be a solution in oil or an aqueous medium, a suspension or an emulsion, or an X agent, a powder, a granule, a tablet or a capsule, and may additionally include a dispersing agent or a stabilizing agent.

Since the composition of the present disclosure improves the cell death of the cancer cells by using the EGFR-targeted agent as the aforementioned susceptibility enhancer and the anticancer agent, the disclosure of the duplicated contents is omitted for avoiding the excessive complexity of this specification.

In still yet another aspect of the present invention, there is provided a method of predicting susceptibility to an EGFR-targeted agent including:

(a) preparing a biological sample from a subject;
(b) measuring an expression level of a RON (Recepteur d'Origine Nantais, NM_002447.1) gene; or an expression or activity level of a protein of the gene in the biological sample; and
(c) determining susceptibility to the EGFR-targeted agent of the subject based on the verified result of the level measured in step (b).

According to the preferred embodiment of the present disclosure, the target has a wild-type gene such as KRAS (V-Ki-ras2 Kirsten rat sarcoma viral oncogene homolog, NM_033360.2), NRAS (neuroblastoma RAS viral (v-ras) oncogene homolog, NP_002515.1), or BRAF (v-raf murine sarcoma viral oncogene homolog B, NP_004324.2).

The prediction method of the present disclosure is constituted by including processes of determining that the corresponding sample has susceptibility to the EGFR-targeted agent when the expression or the activity of the disclosed gene or protein is inhibited or reduced as compared with a normal sample after obtaining a biological sample from a target patient and measuring whether one gene or a plurality of genes selected from the group consisting of the aforementioned genes in the sample is expressed; and determining that the corresponding sample has resistance to the EGFR-targeted agent when the expression or the activity of the disclosed gene or protein is increased or enhanced.

The prediction method of the present disclosure characterizes that whether a specific gene or protein (preferably, an active form) is expressed in the sample is an index of the susceptibility to the anticancer agent of the cancer cells.

According to the preferred embodiment of the present disclosure, in step (b), an expression level of any one gene selected from the group consisting of EGFR (Epidermal Growth Factor Receptor, Gene Bank accession No. U48722.1), Adam11 (ADAM metallopeptidase domain 11, NM_002390.4), Adam32 (ADAM metallopeptidase domain 32, NM_145004.5), FZD4 (Frizzled family receptor 4, NM_012193.2), GPER (G protein-coupled estrogen receptor 1, NM_001505.2), and GPR101 (G protein-coupled receptor 101, NM_054021.1) genes and a combination thereof; an expression or activity level of the protein of the gene is additionally measured.

According to the preferred embodiment of the present disclosure, in step (c), when the expression level of the RON gene; or the expression or activity level of the protein thereof is low as compared with the normal level, it is determined that there is the susceptibility (susceptibility) to the EGFR-targeted agent of the target.

According to the preferred embodiment of the present disclosure, in step (c), when the expression level of the RON gene; or the expression or activity level of the protein thereof is high as compared with the normal level, it is determined that there is the resistance to the EGFR-targeted agent of the target.

According to the preferred embodiment of the present disclosure, when the expression level of any one gene selected from the group consisting of the Adam11, Adam32, FZD4, GPER, GPR101 genes and a combination thereof; an expression or activity level of the protein of the gene is low as compared with a normal level, it is determined that there is the susceptibility (susceptibility) to the EGFR-targeted agent of the target.

More particularly, in step (c) of the present disclosure, based on the result of the expression level measured in step (b), when it is verified that the KRAS, NRAS, or BRAF wild-type gene is included and the level of the activity of the RON gene and the active protein which is the product thereof is inhibited and/or reduced as compared with a normal (wild-type) value, it is determined that the corresponding tumor cells obtained from the target patient has the susceptibility to the EGFR-targeted agent as the anticancer agent. In this case, additionally, when the expression level of any one gene selected from the group consisting of the Adam11, Adam32, FZD4, GPER, and GPR101 genes and a combination thereof; the expression or activity level of the protein of the gene is measured and it is determined that the level is inhibited and/or reduced as compared with a normal (wild-type) value, it is determined that the corresponding tumor cells obtained from the target patient has the susceptibility(susceptibility) to the EGFR-targeted agent as the anticancer agent.

In this specification, the term "low expression" or "low activity" used while mentioning the expression level of the genes is referred to as a value of the biomarker detected in the biological sample obtained from a healthy or normal target or an target as a comparison target or a value or level of the biomarker in the biological sample which is lower than a level range, when the biomarker represents abnormal process, disease, or other conditions in the target or a symptom thereof. Further, the term "low expression" or "low activity" may be referred to as a "differential level", "differential value", or "differently expressed" as compared with the "normal" expression level or value of the biomarker, and includes both a quantitative difference and a qualitative difference in the expression.

According to the preferred embodiment of the present disclosure, the measuring of the expression level of the RON gene; or the expression or activity level of the protein of the gene additionally includes measuring whether a splicing variant or a mutant of the gene is present.

According to the present disclosure, the presence of the variant of the gene or one or more mutants in the gene causes a change of the expression aspect of the gene to have an effect on the susceptibility to the EGFR-targeted agent (see Example 3).

The term "variant" used in this specification means RON isoform generated when an exon site of the corresponding gene is deleted by alternative splicing, and an activity degree of the RON is adjusted by alternative splicing which is one of important processes of the gene expression regulation in eukaryotes.

RONΔ155 (alternatively, RON Delta 155), RONΔ160 (alternatively, RON Delta 160), and RONΔ165 (alternatively, RON Delta 165) used in the present disclosure are generated by skipping of the exons through the splicing and always structurally activated without ligands.

According to the present disclosure, splicing variants in which the exons are deleted by an alternative splicing mechanism of the RON have different sensitivities to the drug according to the expression thereof.

The term "mutant" or "variant" used in this specification includes base substitution, deletion, insertion, amplification, and rearrangement of the nucleotide and the amino acid sequence of the corresponding gene. The nucleotide variant is referred to as a change (for example, insertion, deletion, inversion or substitution of one or more nucleotides, for example, a single nucleotide polymorphism (SNP)), in the nucleotide sequence for a reference sequence (for example, a wild-type sequence). The term includes a corresponding change of a complement of the nucleotide sequence unless exhibited otherwise. The nucleotide variant may be somatic mutation or pattern polymorphism.

Further, the amino acid variant is referred to as a change (for example, insertion, substitution, or deletion one or more amino acids, for example, internal deletion or truncation of N- or C-terminal) of the amino acid sequence as compared with the reference sequence (for example, the wild-type sequence).

In the embodiment of the present disclosure, the mutant is E387A and H424L point mutants in which one amino acid is substituted.

Further, it was verified that the E387 site and the H424 site of the amino acid of the RON protein are sites capable of bound to the EGFR protein.

The detection of the variant may be performed by targeted molecule cloning and sequence analysis by using a well known technique in the art. For example, DNA sequence analysis; primer extending assay including allele-specific nucleotide mixing assay and allele-specific primer extending assay (for example, allele-specific PCR, allele-specific ligation chain reaction (LCR), and gap-LCR); allele-specific oligonucleotide hybridizing assay (for example, oligonucleotide ligation assay); a cleave protection assay that detects mismatched nucleotides in a double strand of nucleic acid by using protection from a cleaver; MutS protein binding analysis; electrophoresis analysis comparing mobility of a variant and a wild type nucleic acid molecule; deformation-gradient gel electrophoresis (DGGE, for example, the same as the literature [Myers et al, (1985) Nature 313:495]); analysis of RNase cleavage in mismatched nucleotide pairs; analysis of chemical or enzymatic cleavage of a hetero double-stranded DNA; mass spectrometry (for example, MALDI TOF); genetic bit analysis (GBA); 5' nucleases assay (for example, TaqMan); and an assay using molecular beacon are included, but the methods are not limited thereto.

The term "biological sample" used in this specification means all samples obtained from the target in which the expression of the biomarker of the present disclosure may be detected.

According to the preferred embodiment of the present disclosure, the biological sample is any one selected from the group consisting of saliva, biopsy, blood, skin tissue, liquid culture, feces, and urine and is not particularly limited thereto, and may be treated and prepared by a method which is generally used in the art.

Since the method of the present disclosure determines that there is the susceptibility by using the aforementioned biomarker, the disclosure of the duplicated contents is omitted for avoiding excessive complexity of this specification.

In yet another aspect of the present invention, there is provided a method of enhancing susceptibility to the EGFR-targeted agent including: administering both of a susceptibility enhancer to the aforementioned EGFR-targeted agent and the EGFR-targeted agent to the target.

Since the method of the present disclosure enhances the susceptibility by using the aforementioned susceptibility enhancer and the EGFR-targeted agent as the anticancer agent, the disclosure of the duplicated contents is omitted for avoiding the excessive complexity of this specification.

Hereinafter, these Examples are only for describing the present disclosure in more detail, and it will be apparent to those skilled in the art that the scope of the present disclosure is not limited to these Examples according to the gist of the present disclosure.

Experimental Method and Condition

Immunoprecipitation Method

In order to analyze a RON active form in a colon cancer cell line, after 500 μg of a lysate of the colon cancer cell line was mixed with 1 μg of an anti-RON antibody, cultured for 12 hours at 4° C., added with 20 μl of a protein-sepharose bead (Santa Cruz Biotehcnology, Santa Cruz, Calif., USA), and then additionally reacted for 2 hours. The immunoprecipitate was washed with a buffer solution (Nondiet P-40 lysis buffer) five times, added and heated with 20 μl of a 2×SDS sample solution, and then western blotting was performed by using anti-RON (Santa Cruz Biotechonology) and anti-phospho-Tyrosine (Cell Signaling, Beverly, Calif., USA) antibodies.

In order to analyze interaction of endogenous RON and EGFR, 300 μg of a lysate of a HCT-8 cell line was mixed with 1 μg of an anti-RON antibody or 1 μg of an anti-rabbit IgG antibody, cultured for 12 hours at 4° C., added with 20 μl of the protein-sepharose bead (Santa Cruz Biotehcnology, Santa Cruz, Calif., USA), and then additionally reacted for 2 hours. The immunoprecipitate was washed with a buffer solution (Nondiet P-40 lysis buffer) five times, added and heated with 20 μl of a 2×SDS sample solution, and then western blotting was performed by using anti-RON (Santa Cruz Biotechonology) and anti-EGFR (Cell Signaling, Beverly, Calif., USA) antibodies. In order to analyze interaction of exogenous RON and EGFR, a Δ160 variant as a RON active form was transfected in a LoVo colon cancer cell line without expressing the RON protein itself, a cell lysate was collected after 48 hours, 300 μg of the cell lysate was mixed with 1 μg of an anti-RON antibody or 1 μg of an anti-rabbit IgG antibody, cultured for 12 hours at 4° C., added with 20 μl of the protein-sepharose bead (Santa Cruz Biotehcnology, Santa Cruz, Calif., USA), and then additionally reacted for 2 hours. The immunoprecipitate was washed with a buffer solution (Nondiet P-40 lysis buffer) five times, added and heated with 20 μl of a 2×SDS sample solution, and then western blotting was performed by using anti-RON (Santa Cruz Biotechonology) and anti-EGFR(Cell Signaling, Beverly, Calif., USA) antibodies.

Microarray Analysis

A Colo320HSR colon cancer cell line without expressing the RON protein was transfected for 48 hours with a construct (plasmid) expressing RON active form Δ160 and/or c-MET. Thereafter, the lysate of the cells was analyzed by a microarray.

Gene Overexpression and Suppression Methods

In order to analyze interaction of exogenous RON and EGFR, a construct expressing A160 as a RON active form was transfected for 48 hours into a LoVo colon cancer cell line in which the RON protein was non-expressed.

In order to analyze the endogenous interaction of RON and EGFR, RON siRNA (small interfering RNA) was transfected for 48 hours in the HCT-8 colon cancer cell line in which RON was activated.

The RON siRNA sequence (SEQ ID NO: 13) is as follows: 5'-ACUUGUAGAGGAGUUUGAUU-3'.

Reverse Transcription (RT)-PCR and Real-Time PCR

In order to perform the RT-PCR, Colo320HSR colon cancer cell line in which the RON was non-expressed was transfected with construct expressing the RONΔ160 as the RON active type form for 48 hours and KM12C colon cancer cell line in which the RON was activated was transfected with the RON siRNA for 48 hours. The RNA was extracted by using trizol (Cat.#15596-026, Life Technologies™), respectively. The extracted RNA was synthesized to cDNA by using a RT-PCR Kit (AccuPower RT PreMix, Bioneer). The difference in expression of the corresponding gene was verified by PCR (AccuPower PCRPreMix, Bioneer) by using the synthesized cDNA and a gene-specific primer and quantified by using a real-time PCR (LightCycler 480 SYBR Green, Roche).

TABLE 1

Primer sequences

| Genes | Forward | Reverse |
|---|---|---|
| Adam11 | 5'-TGGCTTCCTCCT CTGTGTCAA-3' (SEQ ID NO: 1) | 5'-GCACTTCCCTTC ATTGCTGC-3' (SEQ ID NO: 2) |
| Adam32 | 5'-AATGGCAGATTG GAGGGAAATG-3' (SEQ ID NO: 3) | 5'-TTCATAGCAGGC AAATGGAGCA-3' (SEQ ID NO: 4) |
| FZD4 | 5'-TGACTGGCTTGT GCTATGTTGG-3' (SEQ ID NO: 5) | 5'-ATGCCTGAAGTG ATGCCCAC-3' (SEQ ID NO: 6) |
| GPR101 | 5'-GGCAGAATGGAA GCCAAGGA-3' (SEQ ID NO: 7) | 5'-TTGCTGTTACGA CGACTGGGTG-3' (SEQ ID NO: 8) |
| GPER | 5'-ATCGTGCCCTTC GCCATCAT-3' (SEQ ID NO: 9) | 5'-CCAGTCGTGAGG TTTCCTAAGCAG-3' (SEQ ID NO: 10) |
| GAPDH | 5'-AGAAGGCTGGGG CTCATTTG-3' (SEQ ID NO: 11) | 5'-AGG GGC CAT CCA CAG TCT TC-3' (SEQ ID NO: 12) |

TABLE 2

Reverse transcription - PCR (polymerase chain reaction) condition

| 42° C. | 90° C. |
|---|---|
| 60 min | 5 min |

TABLE 3

PCR condition

| 1 cycle | 35 cycle | | | 1 cycle |
|---|---|---|---|---|
| 95° C. | 95° C. | 60° C. | 72° C. | 72° C. |
| 5 min | 30 sec | 1 min | 1 min | 10 min |

TABLE 4

Quantitative real-time PCR condition

| 1 cycle | 50 cycle | | | 1 cycle |
|---|---|---|---|---|
| 95° C. | 95° C. | 58° C. | 72° C. | 72° C. |
| 5 min | 30 sec | 30 sec | 1 min | 10 min |

Western Blot

In order to perform the western blot, a protein separated from each cell was separated through SDS-PAGE and transferred to polyscreen membranes (New England Nuclear, Boston, Mass., USA), reacted for 12 hours at 4° C. by using various antibodies (anti-phospho RON (MyBioSource, San Diego, Calif., USA), anti-phospho Tyrosine, anti-EGFR, anti-phospho EGFR (Cell signaling Technology, Beverly, Mass., USA), anti-RON, and anti-r-tubulin (Santa Cruz Biotechnology), and then washed with a 1×TBS-T buffer solution for 10 minutes three times. A suitable anti-rabbit-HRP or anti-mouse-HRP secondary antibody reacted for 2 hours at room temperature and was washed with the 1×TB S-T buffer solution for 10 minutes three times to verify the expression of the protein by using an ECL solution (Amersham, Buckinghamshire, UK).

Phospho-RTK Array

After the Δ160 construct as the RON active form was transfected for 48 hours in the Colo320HSR cell line without expressing the RON protein, the cell lysate was collected. 50 μg of the collected cell lysate was reacted with a membrane included in a human phospho-RTK array kit (R&D Systems, Inc., Minneapolis, Minn., USA) for 12 hours at 4° C., washed with a TBS-T buffer solution three times, reacted with an anti-phospho-Tyrosine HRP antibody for 2 hours at room temperature, and then washed with the TB S-T buffer solution three times. Thereafter, in the membrane, a change in the expression of receptor tyrosine kinase (RTK) proteins was verified by using the ECL solution (Amersham, Buckinghamshire, UK).

Treatment of Anticancer Agent

Figure 3A:
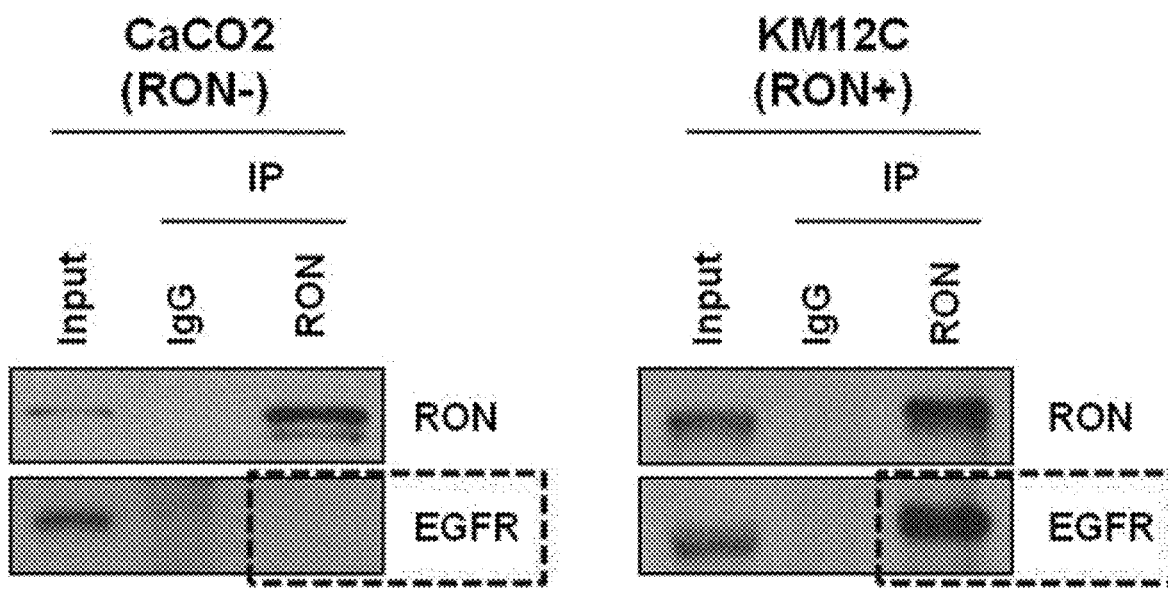
FIG. 3A illustrates an analysis result of endogenous intracellular binding between the RON protein and the EGFR protein.

After 5, 10, and 20 μg/ml of cetuximab (Merck & Co., Inc, NJ, USA) were treated for 48 hours in CaCo2 and LIM1215 colon cancer cell lines in which the RON was not activated and a KM12C cell line in which the RON was activated, a cell solution was collected to perform trypan blue counting (FIG. 3A).

KM12C colon cancer cell line in which the RON was activated was treated with RON siRNA for 48 hours, was treated with 20 μg/ml of cetuximab for 48 hours, and then the cell solution was collected to perform trypan blue counting.

Treatment of Inhibitor

3 μm of an RON inhibitor (LY2801653) and 20 μg/ml of an EGFR-targeted agent (cetuximab) were treated for 48 hours in the KM12C colon cancer cell line in which the RON was activated. After treatment, the cell lysate was collected to perform trypan blue counting.

Further, narnatumab (Creative Diagnostic#TAB-184 Anti-Human RON Therapeutic Antibody) as an RON-target antibody anticancer agent and 100 μg/ml of an EGFR-targeted agent (cetuximab) were treated for 48 hours. After treatment, the cell death induction degree was verified by the same method as above.

Mutagenesis of Point Mutant

The mutagenesis was performed according to a guideline provided from the kit by using a muta-Direct mutagenesis kit (Intron, Cat No. 15071). Primer sequences used in mutagenesis are as follows.

```
RON (E387A);
Forward:
5'-GGA GCG CTG TTG TGC ATC CCC AGT CCA TCC-3',

Reverse:
5'-GGA TGG ACT GGG GAT GCA CAA CAG CGC TCC-3',
```

-continued

RON (H424L);
Forward:
5'-ACA CCA GCT GCC GCC TCT TCC CTC TGC TGG-3',

Reverse:
5'-CCA GCA GAG GGA AGA GGC GGC AGC TGG TGT-3',

RON (K1114M);
Forward:
5'-AAT GTG CCA TCA TGT CAC TAA GTC G-3',

Reverse:
5'-CGA CTT AGT GAC ATG ATG GCA CAT T-3',

EGFR (D813N);
Forward:
5'-TTG GTG CAC CGC AAC CTG GCA GCC AGG-3',

Reverse:
5'-CCT GGC TGC CAG GTT GCG GTG CAC CAA-3'.

Mutation was progressed by using the primer and a muta-direct enzyme and then transformation was progressed in E-Coli. After DNA was extracted from colonies, mutation was verified through a sequencing analysis method.

RON Activity Analysis in Colon Cancer Cell Line or Colon Cancer Patient's Tissue In order to analyze the RON activity, after a protein was extracted from a cell line or a colon cancer patient's tissue (by using a RIPA buffer), activity was verified by using a phospho-RON antibody (Mybiosource, MBS462024, dilution factor 1:1000) in 20 μg of the cells and 50 μg of the colon cancer patient's tissue.

Further, after immunoprecipitation was performed with the RON antibody (santa cruz; sc-322, Lot#G1514, 2 μg, incubation of 2 days) (by using 300 μg of the cell line and the colon cancer patient's tissue), phosphorylation was verified by a phospho-tyrosine antibody (Cell signaling; 9411, dilution factor 1:1000). In order to verify RONΔ155 and RONΔ160 (alternative splicing form) which were the RON active forms, RNA was extracted from the colon cancer cell line or the colon cancer patient's tissue with a trizol reagent. After analyzing the cDNA, analysis was performed by using two primers.

First, a primer designed for distinguishing RONΔ155 and RONΔ160 was used and the primer was as follows: Forward:5'-CTCTGGGGACCAGGTTTTCC-3', Reverse:5'-ACCATCAATGGCAGGGAGTG-3'. In the RT-PCR condition, 37 cycles were performed for 5 minutes at 94° C., for 30 seconds at 94° C., for 30 seconds at 63° C., and for 1 minute 30 seconds at 72° C. and extended for 10 minutes at 72° C. RON wild type was verified 1552 bp, RONΔ155 was verified 1078 bp, and RONΔ160 was verified 1225 bp.

In order to further verify the RT-PCR condition, the primers reported in an existing literature were used and the primers were as follows. Forward: 5'-TGG TCA GTA GCA GCT TCT CA-3', Reverse: 5'-AGG CAG CAG GAT ACC AAG GA-3'. In the RT-PCR condition, 38 cycles were performed for 5 minutes at 94° C., for 30 seconds at 94° C., for 45 seconds at 57° C., and for 1 minute at 72° C. and extended for 10 minutes at 72° C. RON wild type was verified 1.6 kb, RONΔ160 was verified 1.3 kb, and RONΔ155 was verified 1.1 kb.

Example 1. Activity of EGFR According to Activity of RON Protein 1-1. Presence of RON Protein Active Form in Human Colon Cancer Cell Line The present inventors selected a colon cancer cell line in which the RON protein was activated or de-activated and verified the RON phosphorylation in a total of 19 human colon cancer cell lines by using western blotting.

The phosphorylated RON protein was regarded as the RON active form protein.

As a result, as illustrated in FIG. 1A, in four cell lines HT-29, KM12C, KM12L4, and SW1417 among 18 cell lines, the expression of the phosphorylated RON protein was observed and it can be seen that the four cell lines had the RON activity.

Meanwhile, in the LoVo and Colo320HSR colon cancer cell lines, it was exhibited that the RON protein was absent.

1-2. Analysis of Gene Expression According to Activation of RON Protein Using DNA Microarray Analysis In order to analyze the gene expression level according to the RON expression in the Colo320HSR cell line in which the RON protein was absent, the present inventors simultaneously overexpressed the Δ160 variant which was active form of both MET and RON in the Colo320HSR cell and then performed the microarray.

The overexpression of the RON gene was considered as the activation of the RON gene or protein.

Figure 1B:
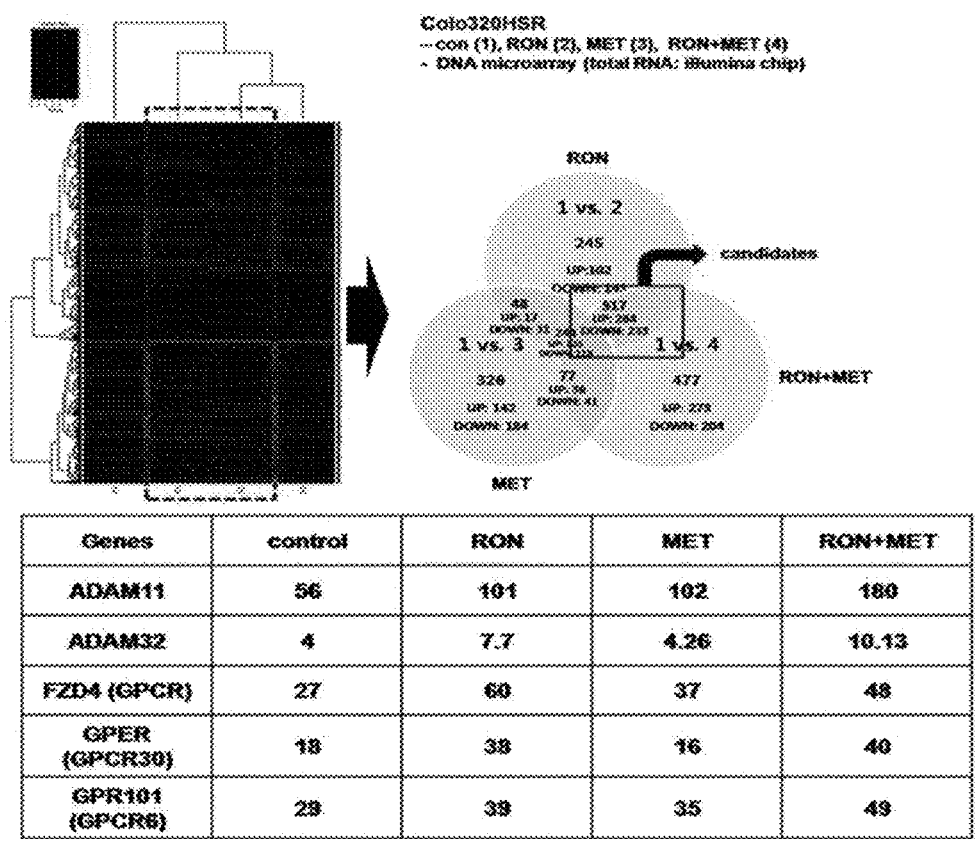
FIG. 1B illustrates an analysis result of genes changed by only RON genes.

As illustrated in FIG. 1B, the genes changed by only the RON activation were analyzed by comparing with genes in a sample group which were overexpressed only the MET gene, and as a result, five genes Adam11, Adam32, FZD4, GPER, and GPR101 associated with the EGFR were identified as the genes changed by the RON.

1-3. Real-Time Polymerase Chain Reaction (PCR) Analysis of EGFR Transactivation-Related Genes According to RON Activation in Colon Cancer Cell Line In order to analyze the expression level change of the EGFR transactivation-related genes according to the RON activation, the present inventors performed the real-time PCR with respect to the five genes (Adam11, Adam32, FZD4, GPER, and GPR101) associated with the EGFR transactivation which was estimated that the expression was changed by the RON, after the Δ160 variant as the RON activation form was overexpressed in the Colo320HSR colon cancer cell line in which the RON was not expressed.

Figure 1C:
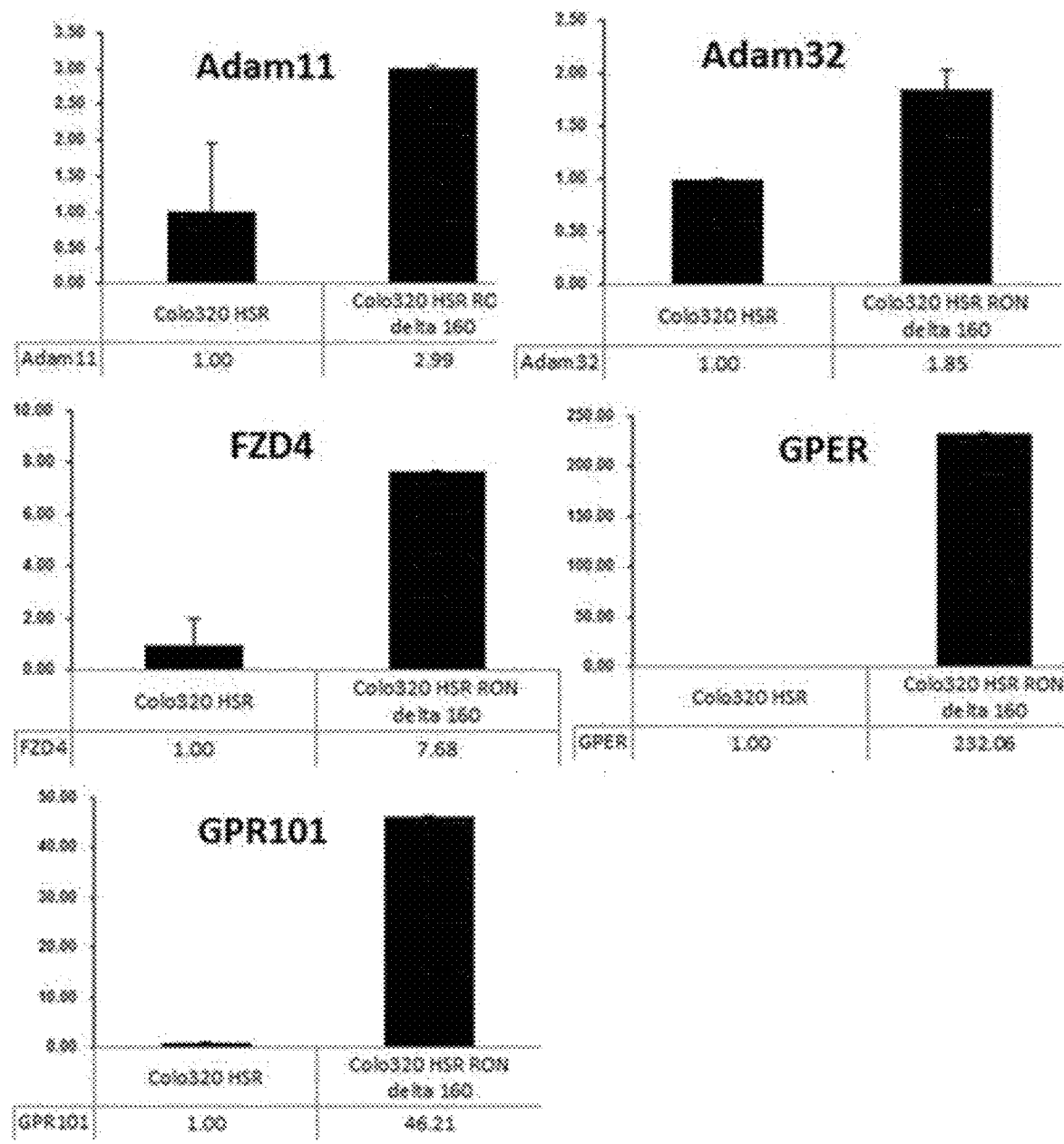
FIG. 1C illustrates a real-time PCR analysis result of genes related with EGFR transactivation by RON activation.

As a result, as illustrated in FIG. 1C, it was observed that the expression of the Adam11, Adam32, FZD4, GPER, and GPR101 genes was significantly increased by RON overexpression.

1-4. RT-PCR (Reverse Transcription Polymerase Chain Reaction) Analysis of EGFR Transactivation-Related Genes According to RON Activation in Colon Cancer Cell Line In order to analyze the expression level change of the EGFR transactivation-related genes according to the RON activation, the inventors performed the PCR with respect to the five genes Adam11, Adam32, FZD4, GPER, and GPR101 associated with the EGFR transactivation which was estimated that the expression was changed by the RON, after the Δ160 variant as the RON activation form of the RON gene was overexpressed in the Colo320HSR colon cancer cell line in which the RON was not expressed.

Figure 1D:
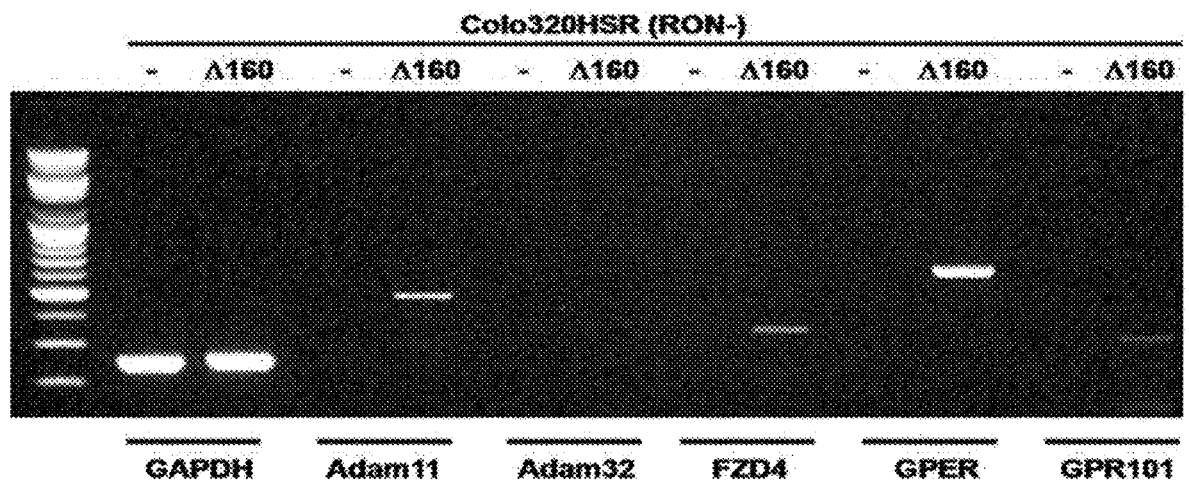
FIG. 1D illustrates an RT-PCR expression analysis result of genes related with EGFR transactivation by RON activation.

As a result, as illustrated in FIG. 1D, by the RON activation, it was observed that the expression of the Adam11, Adam32, FZD4, GPER, and GPR101 genes was significantly increased in the sample group in which the Δ160 variant as the RON activation form of the RON gene was overexpressed.

1-5. Real-Time PCR Analysis of EGFR Transactivation-Related Genes in Colon Cancer Cell Line in which RON is Inhibited The inventors analyzed the expression of the genes Adam11, Adam32, FZD4, GPER, and GPR101 associated with the EGFR transactivation with real-time PCR after artificially suppressing the RON activity by using an siRNA technique in the KM12C colon cancer cell line in which the RON was activated, in order to analyze the change aspect of the expression of the EGFR transactivation-related genes according to the RON inhibition.

Figure 1E:
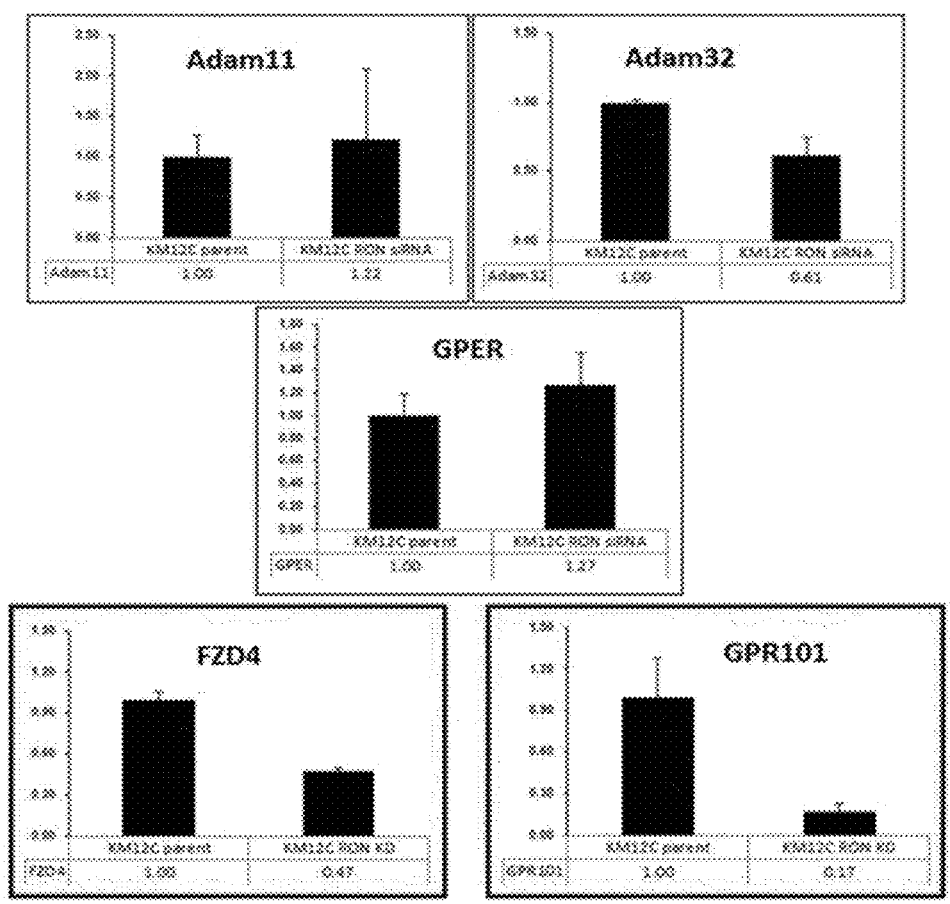
FIG. 1E illustrates a real-time PCR analysis result of genes related with EGFR transactivation by RON inhibition.

As a result, as illustrated in FIG. 1E, it was exhibited that the FZD4 and GPR101 genes were significantly reduced by inhibition of the RON activation.

1-6. Analysis of Activity of EGFR Protein by RON Activation

As described above, it was verified that the EGFR transactivation-related genes which were identified in Example 1-2 (FIG. 1B) and verified in Examples 1-3 to 1-5 (FIGS. 1C to 1E) was expressed by the RON activation. Accordingly, the inventors verified whether the phosphorylated protein of the EGFR was expressed by using western blotting after overexpressing the Δ160 variant as the RON activation form in the Colo320HSR colon cancer cell line in which the RON was not expressed in order to verify whether the activation of the EGFR protein was induced according to actual RON activation.

Figure 1F:
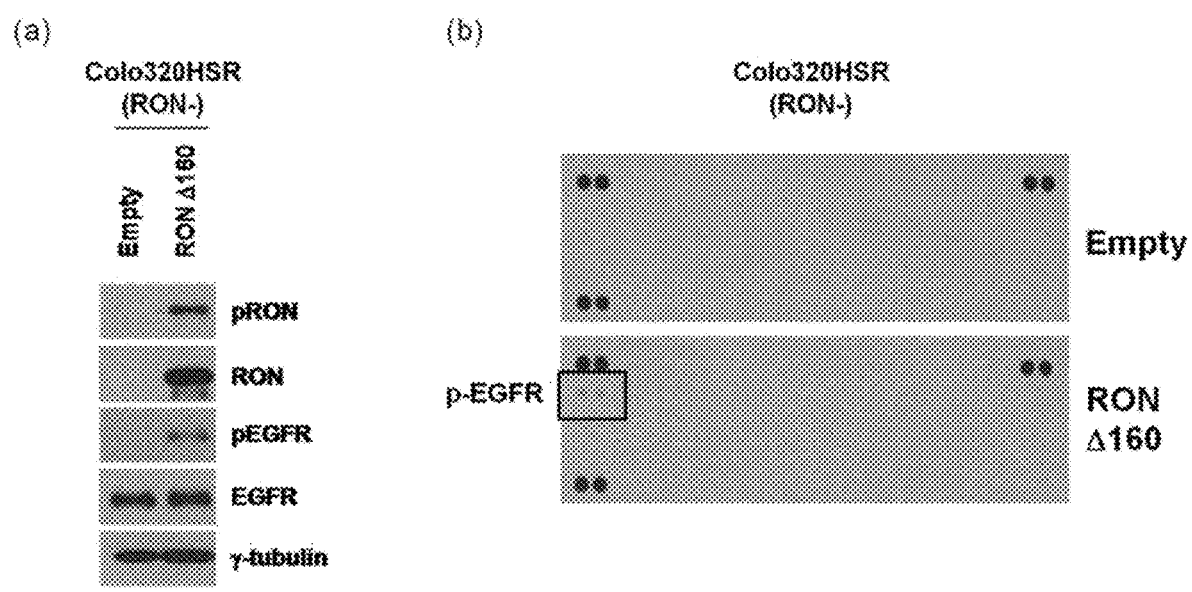
FIG. 1F illustrates an analysis result of activation of EGFR proteins by RON activation.

As a result, as illustrated in FIG. 1F, when the RON was activated, it was verified that the phosphorylated protein of the EGFR was increased (a), and it was verified that the phosphorylation of the EGFR was induced through an RTK-protein array after overexpressing the Δ160 variant as the RON activation form. Accordingly, it was seen that the activity of the EGFR was induced according to the activation of the RON.

Example 2. Change of EGFR Activity According to RON Activity 2-1. Activation of EGFR Protein by Activation of RON Protein The inventors performed western blot, after overexpressing the Δ160 variant as the activation form of the RON gene in the LoVo and Colo320HSR colon cancer cell lines in which the RON was not expressed in order to verify the activation of the EGFR protein by the RON activation.

Figure 2A:
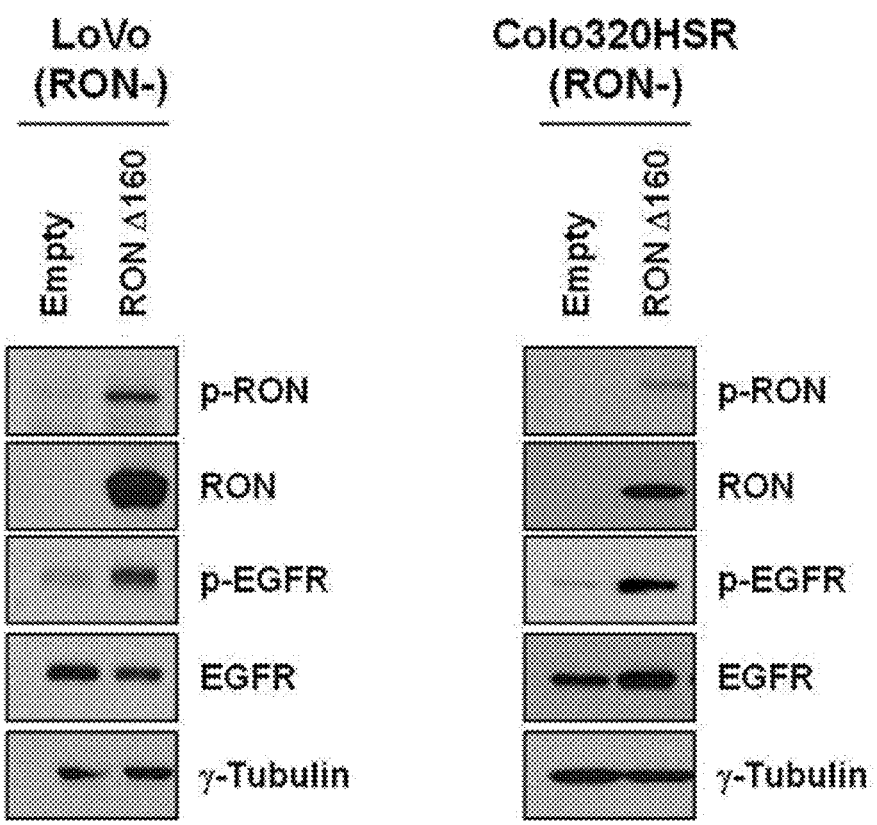
FIG. 2A illustrates an induced phosphorylation result of EGFR by RON activation.

As a result, as illustrated in FIG. 2A, it was verified that the activity of the EGFR was increased according to the RON activation.

2-2. Change in Activity of EGFR Protein by RON Inhibition

The inventors verified the phosphorylation induction of the EGFR by performing the western blot, after artificially suppressing the RON by using a siRNA technique in the KM12C and HT29 colon cancer cell lines in which the RON was expressed and activated, in order to verify the change in activity of the EGFR protein by the activation of the RON protein.

Figure 2B:
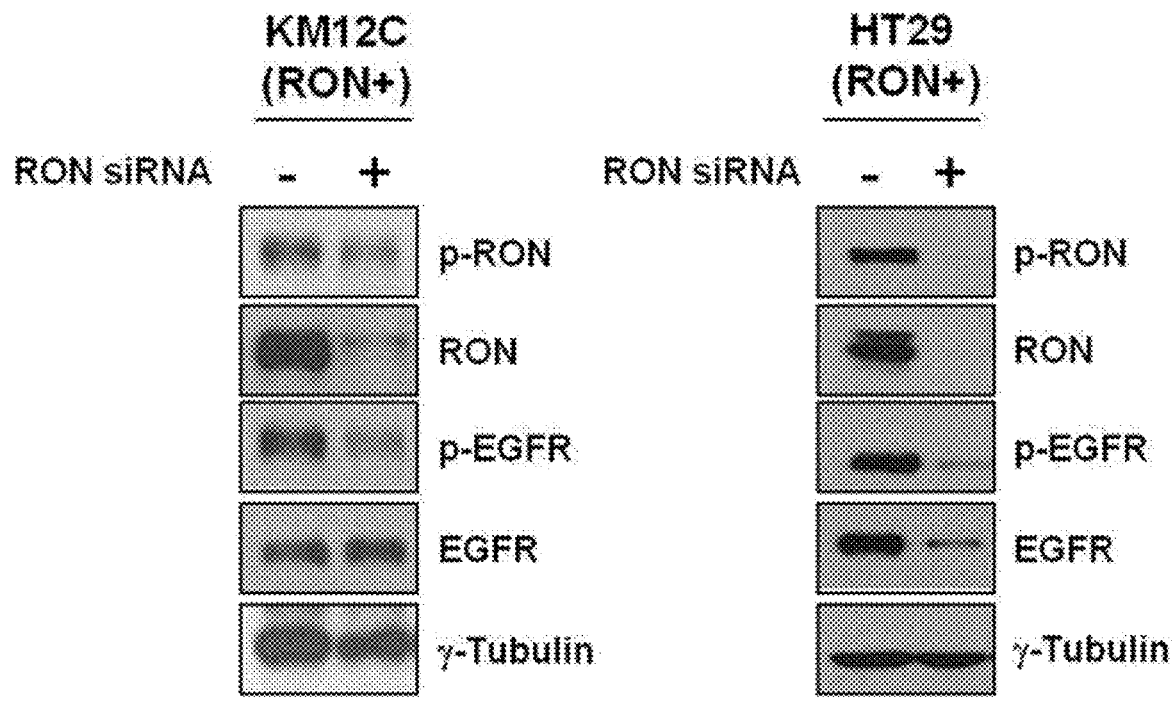
FIG. 2B illustrates an analysis result of a change in activation of EGFR proteins by RON inhibition.

As a result, as illustrated in FIG. 2B, it was verified that the activity of the EGFR was also decreased according to the RON inhibition.

2-3. Change in Activity of EGFR Ligand-Dependent EGFR by RON Inhibition

The inventors verified the phosphorylation degree of the EGFR according to an EGF ligand treating time which induces the activity of the EGFR, after inhibiting the RON by using the siRNA technique in the KM12C colon cancer cell line in which the RON was expressed and activated in order to verify the change in the activity of EGFR ligand-dependent EGFR.

Figure 2C:
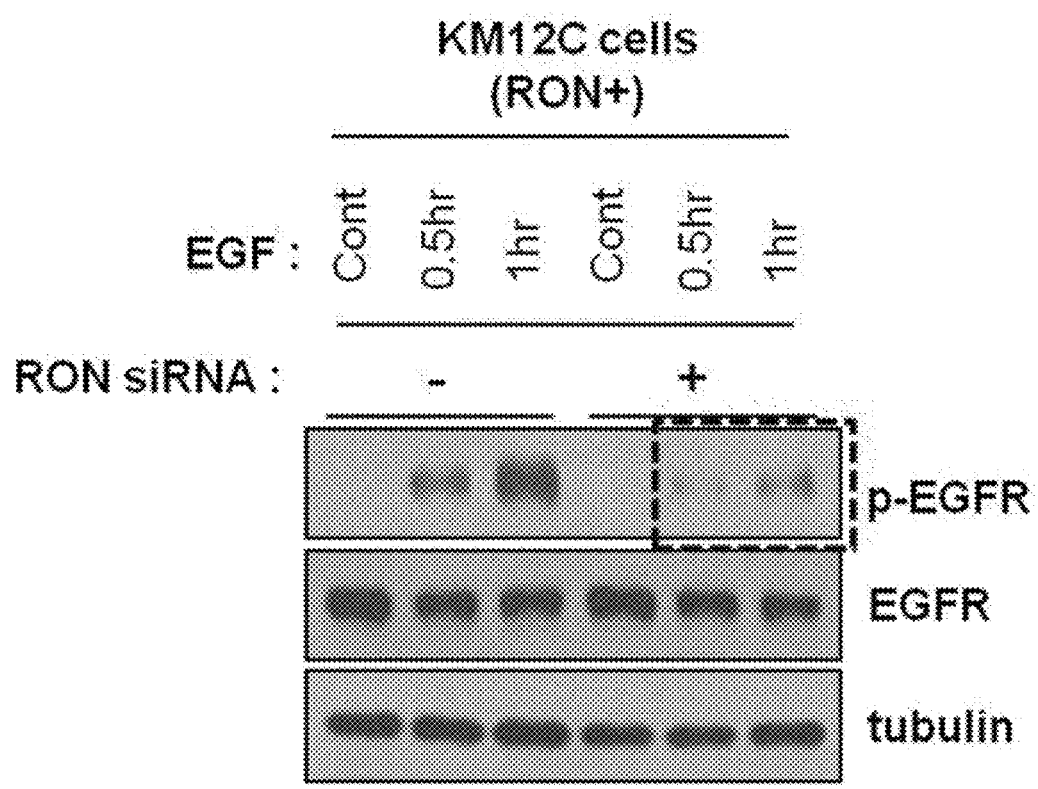
FIG. 2C illustrates an analysis result of a change in EGFR ligand-independent EGFR activation by RON inhibition.

As a result, as illustrated in FIG. 2C, it was verified that the phosphorylation of the EGFR induced by the EGF was decreased and the activity was decreased according to the RON inhibition.

Example 3. Drug Susceptibility Analysis of Cetuximab According to Activation of Ron Protein 3-1. Analysis of Binding in Endogenous Cells Between RON Protein and EGFR Protein The inventors observed presence or absence of the binding between the RON protein and the EGFR protein by immunoprecipitation by using the RON antibody in order to analyze the presence or absence of the binding between the RON protein and the EGFR protein in the cells of the CaCO2 colon cancer cell line in which the RON was not activated and the KM12C colon cancer cell line in which the RON was activated.

As a result, as illustrated in FIG. 3A, it can be seen that in the CaCO2 cell in which the RON was not activated, the binding between the RON protein and the EGFR protein was not made, and in the KM12C cell in which the RON was activated, the binding between the RON protein and the EGFR protein was made.

3-2. Analysis of Binding in Exogenous Cells Between RON Protein and EGFR Protein The inventors observed presence or absence of the binding between the RON protein and the EGFR protein by immunoprecipitation by using the RON antibody, after respectively overexpressing a RON normal gene and an EGFR normal gene and simultaneously overexpressing the RON normal gene and the EGFR normal gene in the colon cancer cell line CaCO2 in which the RON was not activated.

Figure 3B:
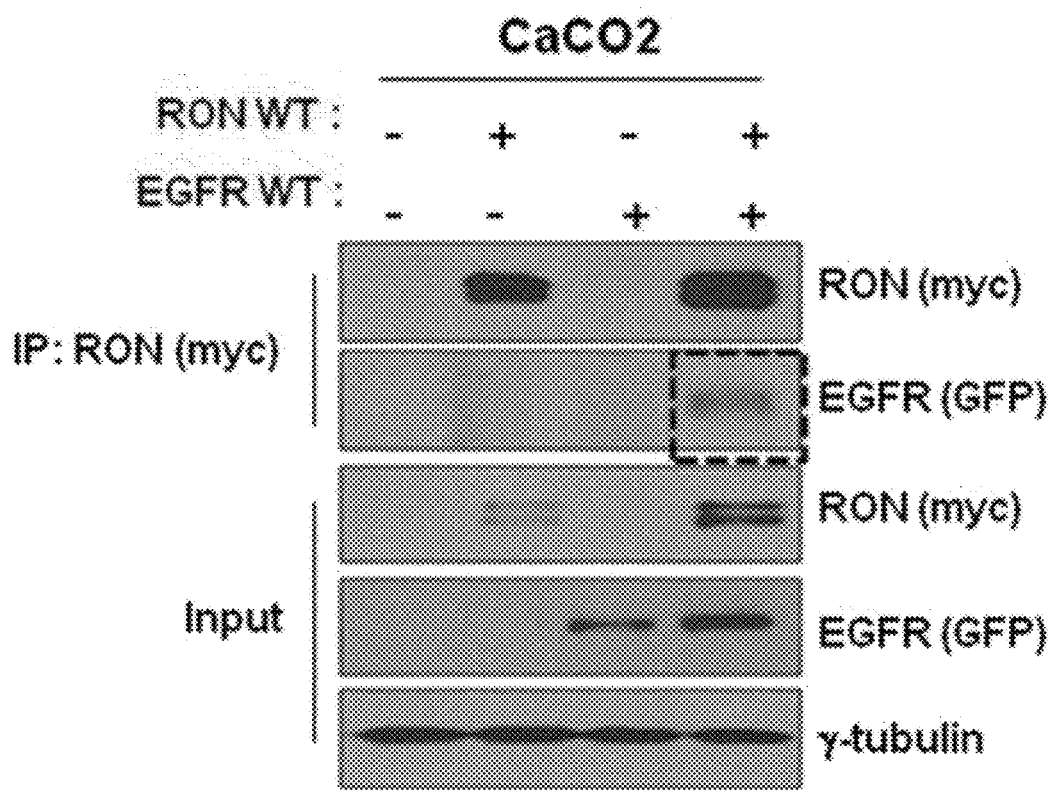
FIG. 3B illustrates an analysis result of exogenous intracellular binding between the RON protein and the EGFR protein.

As a result, as illustrated in FIG. 3B, it can be seen that the binding between the RON protein and the EGFR protein was made in the case of simultaneously overexpressing the RON normal gene and the EGFR normal gene.

3-3. Analysis of EGFR Protein Domain Bound to RON Protein Through In Vivo Full Down Assay The inventors observed a domain of the EGFR bound to the RON protein through immunoprecipitation by using the RON antibody after respectively overexpressing a RON protein, a kinase domain protein of the EGFR, and an extracellular domain (EC) protein and simultaneously overexpressing the RON and the kinase domain protein of the EGFR in a 293T cell line in which the RON and the EGFR were not expressed, not the colon cancer cell line.

Figure 3C:
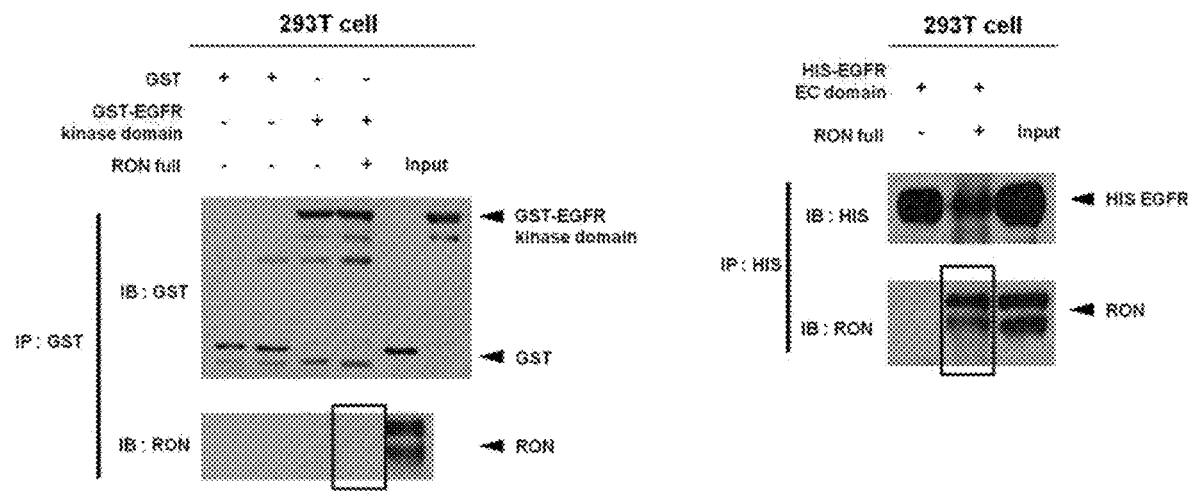
FIG. 3C illustrates an analysis result of an EGFR protein domain bound with the RON protein through an in vivo full down assay.

As a result, as illustrated in FIG. 3C, it can be seen that the RON and the EC protein of the EGFR were bound to each other.

3-4. Analysis of Domain of EGFR Protein Bound to RON Protein Through In Vitro Cell Free Full Down Assay The inventors observed presence or absence of binding between the RON normal protein and the active form Δ160 protein by reacting with the kinase domain protein and the EC protein of the EGFR by using an in vitro cell free full down assay, in order to re-verify binding between the RON protein and the EC protein of the EGFR.

Figure 3D:
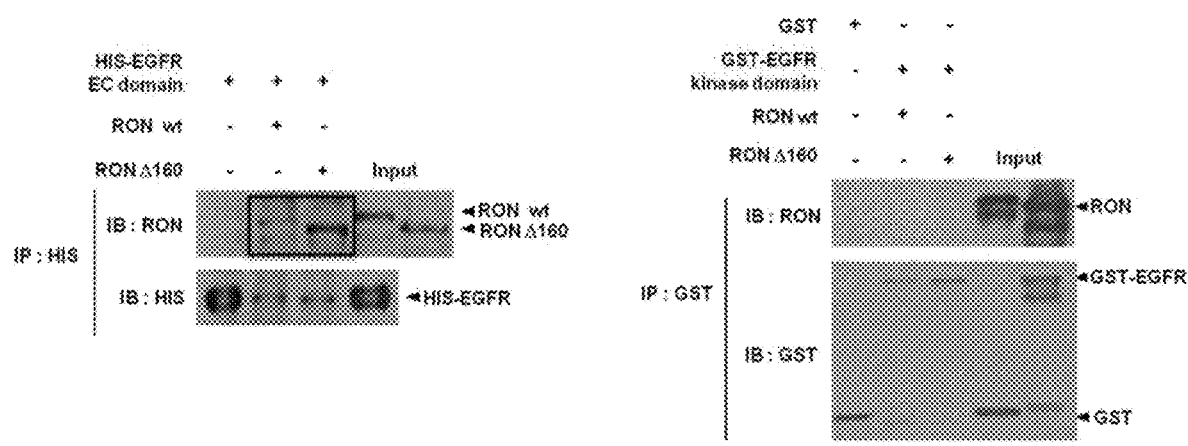
FIG. 3D illustrates an analysis result of an EGFR protein domain bound with the RON protein through an in vitro cell free full down assay.

As a result, as illustrated in FIG. 3D, it can be seen that both the RON normal protein and the active form Δ160 protein bound to the EC protein of the EGFR.

3-5. Analysis of Prediction of RON Protein Binding Site Bound to EGFR Protein Using Computer Modeling The inventors predicted that a binding site of the RON bound to the EGFR by introducing a construct of the EGFR protein and a construct of the RON protein by using a computer modeling system, in order to analyze a main binding site of the RON bound to the EGFR protein.

Figure 3E:
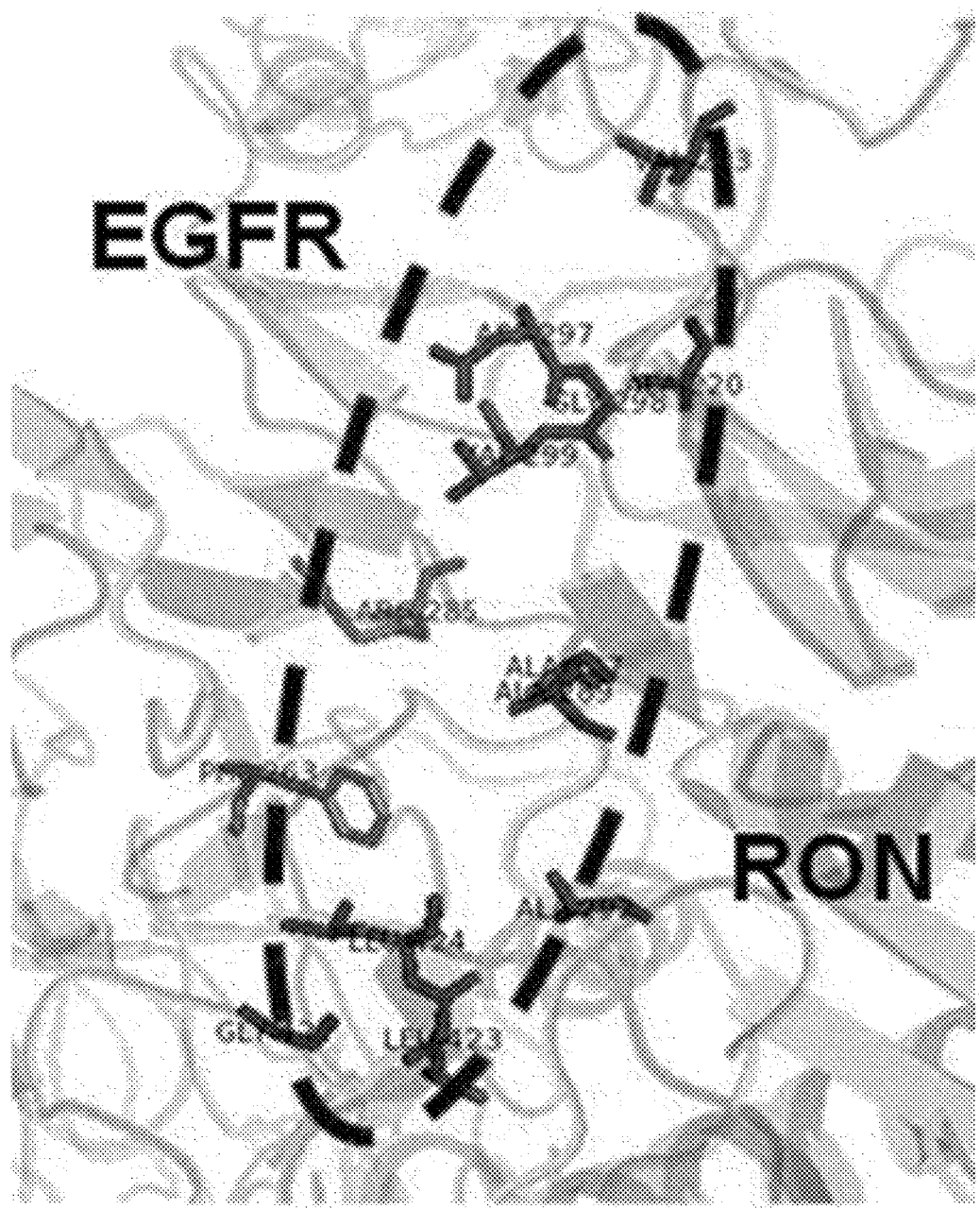
FIG. 3E illustrates an analysis result of predicting an RON protein binding site bound with the EGFR protein using computer modeling.

As a result, as illustrated in FIG. 3E, an E387 site and a H424 site of the amino acid of the RON protein were predicted and analyzed as sites which may be bound to the EGFR protein.

3-6. Analysis of Binding Site of RON Protein Bound to EGFR Protein

The inventors observed binding between normal form, active form, and mutant form RON proteins and the EGFR protein through immunoprecipitation by using the RON antibody after respectively overexpressing the RON normal form gene, the active form Δ160, and E387A and H424L point mutant genes of the RON and simultaneously overexpressing the EGFR gene in the 293T cell line in which the RON and the EGFR were not expressed, in order to analyze the main binding site of the RON bound to the EGFR protein.

Figure 3F:
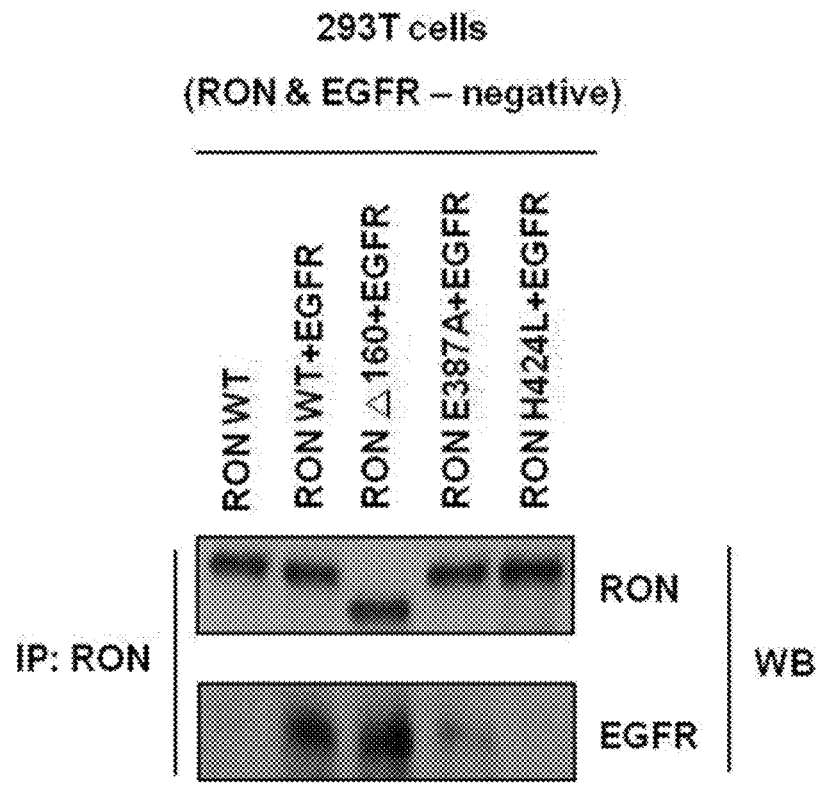
FIG. 3F illustrates an analysis result of an RON protein binding site bound with the EGFR protein.

As a result, as illustrated in FIG. 3F, the binding was verified in the normal form, the active form, and the E387A mutant form of the RON, and in the H424L mutant form of the RON, the binding of the EGFR protein was not verified.

3-7. Analysis of EGFR Activity According to Binding Site of RON Protein Bound to EGFR Protein The inventors verified the phosphorylation of the EGFR as the activity of the EGFR through western blot by respectively overexpressing the RON normal form gene and the active form Δ160 variant and the H424L mutant gene verified in Example 3-6 (see FIG. 3F) and simultaneously overexpressing the EGFR normal form gene in the 293T cell line in which the RON and the EGFR were not expressed, in order to analyze the EGFR activity according to the binding site of the RON bound to the EGFR protein.

Figure 3G:
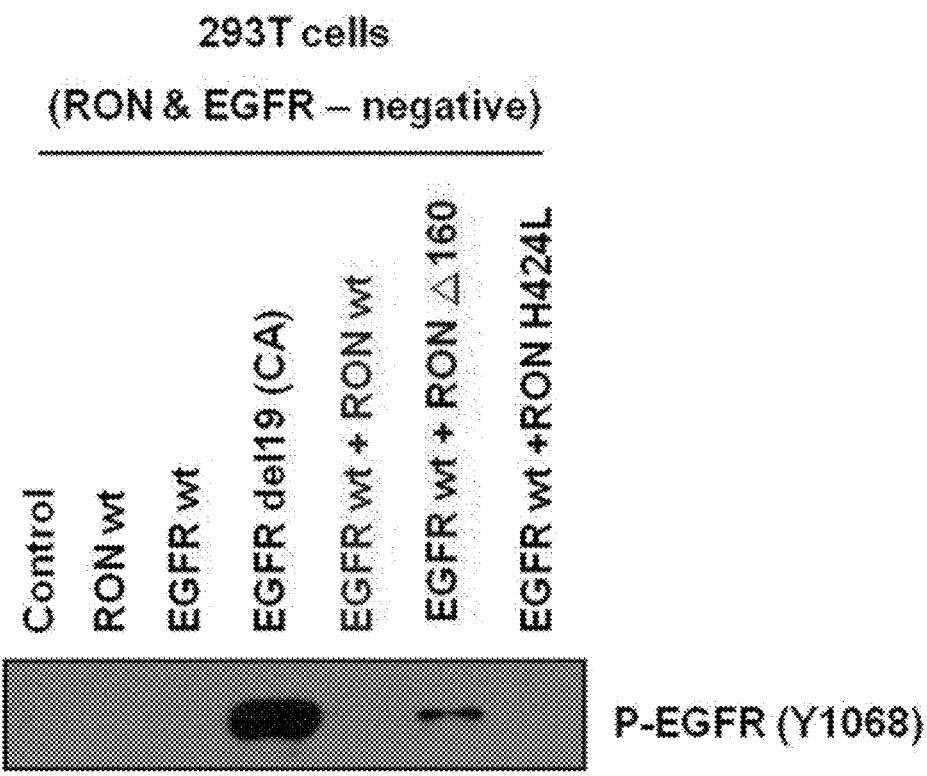
FIG. 3G illustrates an analysis result of EGFR activation according to a binding site of the RON protein bound with the EGFR protein.

As a result, as illustrated in FIG. 3G, like the EGFR active form mutant (EGFR del19), only in the place simultaneously overexpressing the EGFR normal form, the active form Δ160 variant of the RON, phosphorylation of the EGFR was induced, in the normal form of the RON and the H424L mutant form, the phosphorylation of the EGFR was not induced, and the activity of the EGFR was exhibited according to the activation of the RON.

Example 4. Analysis of Activity of EGFR According to RON Activity 4-1. Analysis of Ligand-Dependent EGFR Activity According to RON Active Form Protein The inventors analyzed the EGFR activity by EGF which is a ligand of EGFR according to presence of the active form Δ160 protein of the RON after overexpressing the normal form protein of the EGFR and the kinase dead protein of the EGFR in the 293T cell line in which the RON and the EGFR were not expressed.

Figure 4A:
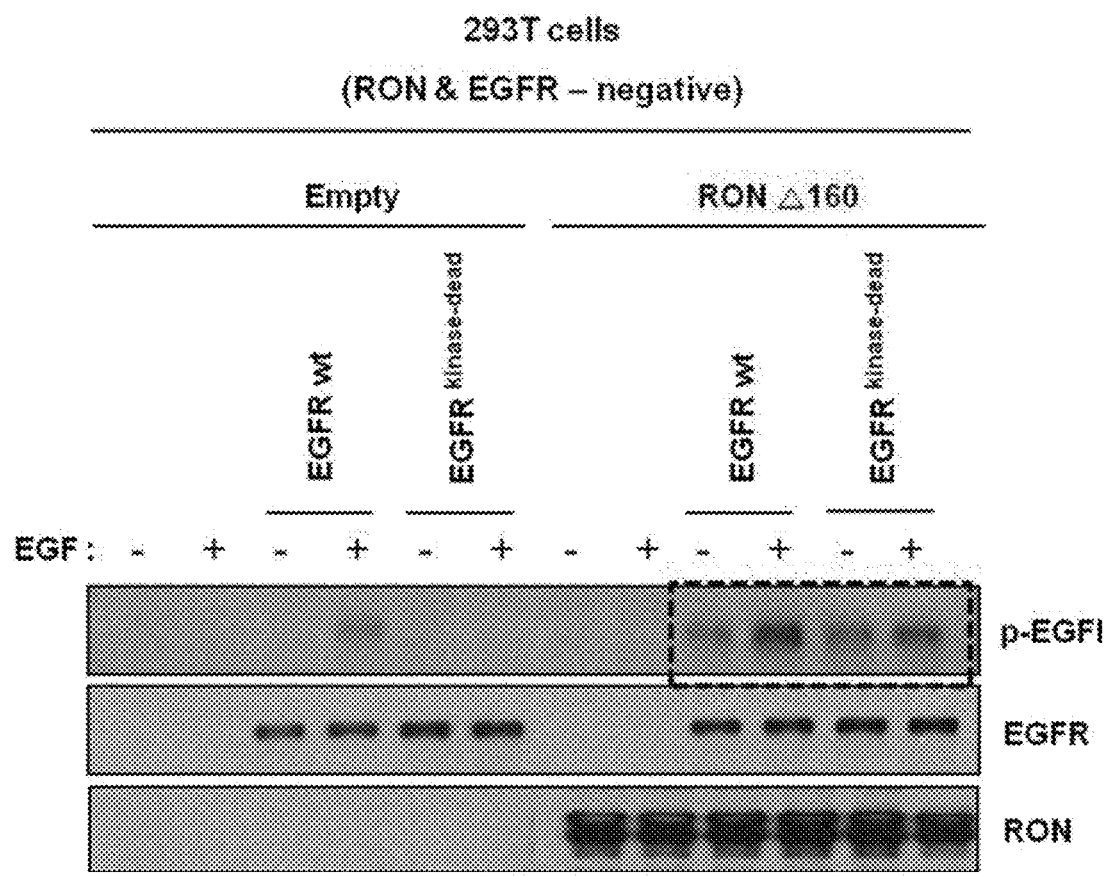
FIG. 4A illustrates an analysis result of presence or absence of ligand-independent EGFR activation according to presence or absence of an RON active form protein.

As a result, as illustrated in FIG. 4A, in the case where the active form Δ160 of the RON was not present, only in the normal form protein of the EGFR, the activation of the EGFR was verified by EGF, in the case where the active form Δ160 protein of the RON was present, the activation of the EGFR was observed regardless of the EGF and the EGFR kinase dead protein, and thus, it can be seen that the active form Δ160 protein of the RON induced the activation of the EGFR ligand-independently of the EGFR.

4-2. Analysis of Ligand-Dependent EGFR Activity According to Ligand-Dependent Activity of RON The inventors analyzed the EGFR activity by EGF which is a ligand of EGFR according to presence of MSP which is a ligand inducing the activity of the RON after overexpressing the normal form protein of the EGFR and the kinase dead protein of the EGFR in the 293T cell line in which the RON and the EGFR were not expressed.

Figure 4B:
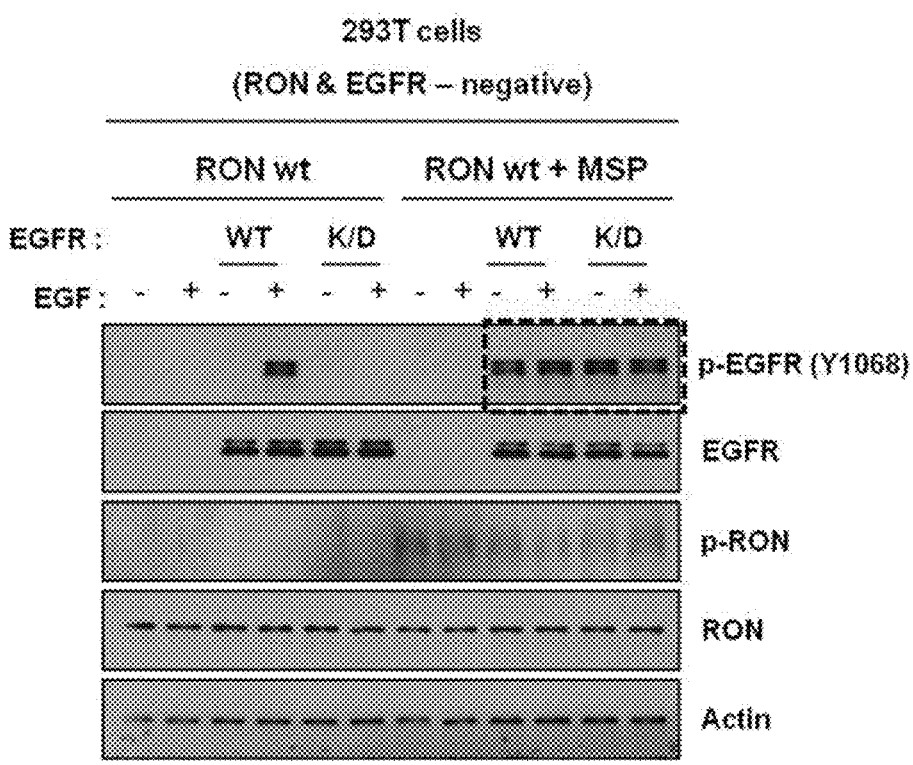
FIG. 4B illustrates an analysis result of presence or absence of ligand-independent EGFR activation according to presence or absence of ligand-independent activation of RON.

As a result, as illustrated in FIG. 4B, in the case where the MSP as the ligand inducing the activity of the RON was not present, only in the normal form protein of the EGFR, the activation of the EGFR was verified by EGF, in the case where the MSP as the ligand inducing the activity of the RON was present, the activation of the EGFR was observed regardless of the EGF and the EGFR kinase dead protein, and thus, it can be seen that if the RON was the active form by the MSP as the ligand inducing the activity of the RON, the activation of the EGFR was induced ligand-independently of the EGFR.

Figure 4C:
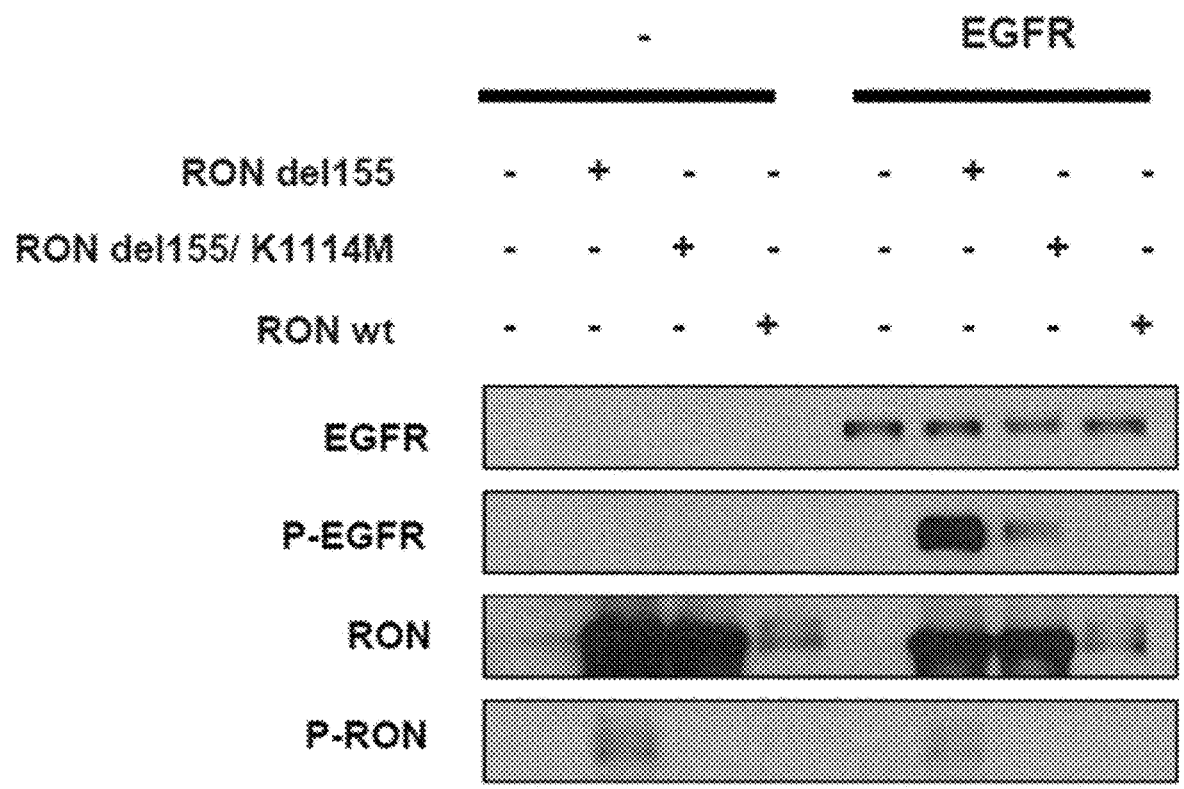
FIG. 4C illustrates an analysis result of the activity of EGFR upon overexpression of RON del155, RON del155/K1114M, and EGFR.

Further, as illustrated in FIG. 4C, when RONΔ155/K1114N (kinase activity inhibition form as a kinase dead RON mutant) and EGFR were overexpressed, it can be seen that the activity of EGFR was reduced as compared with a case where only the active form of the RON was overexpressed.

Figure 9:
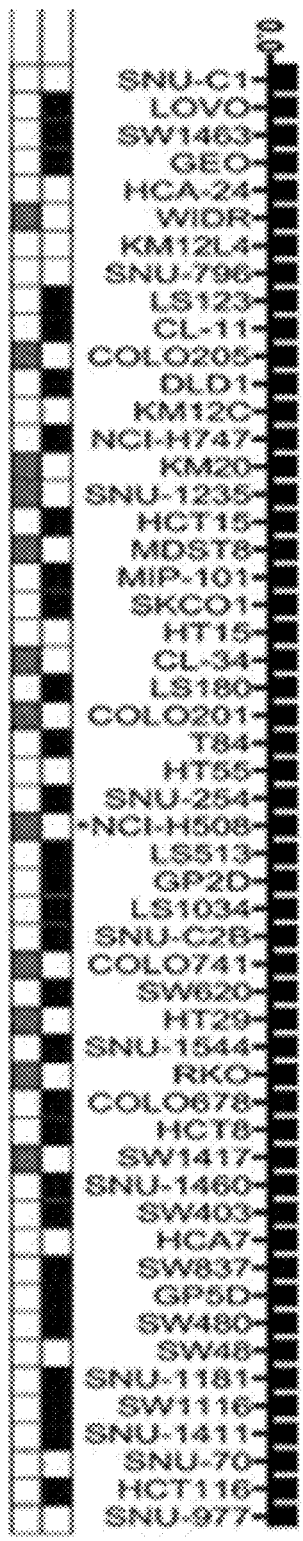
FIG. 9 is a table illustrating that it was known that the KM12C colon cancer cell line had the KRAS, NRAS, and BRAF wild type genes and had resistance to cetuximab (the left-most column indicating BRAF V600E mutation and the adjacent column to the right indicating KRAS mutation).

Example 5. Analysis of EGFR Activity and Association for Cetuximab According to RON Activity 5-1. Analysis of Activity Inhibition of EGFR Through RON Activity Inhibition and EGFR Activity Inhibition for Cetuximab As listed in FIG. 9, it was known that the KM12C colon cancer cell line had the KRAS, NRAS, and BRAF wild type genes and had resistance to cetuximab (Todd M. et al, Dual Pharmacological Targeting of the MAP Kinase and PI3K/mTOR Pathway in Preclinical Models of Colorectal Cancer. PLOS 2014, Volume 9, Issue 11, e113037).

Hereinabove, the inventors verified in Example 1-1 that the RON was activated in the KM12C colon cancer cell line.

Accordingly, the activation degree of the EGFR was observed by western blot by treating cetuximab for each time after artificially inhibiting the RON by an siRNA technique in the KM12C colon cancer cell line which had KRAS, NRAS, and BRAF wild type genes, had resistance to cetuximab and in which the RON was activated, as described above, in order to analyze the activity inhibition of the EGFR through the RON activity inhibition and the EGFR activity inhibition for cetuximab.

Figure 5A:
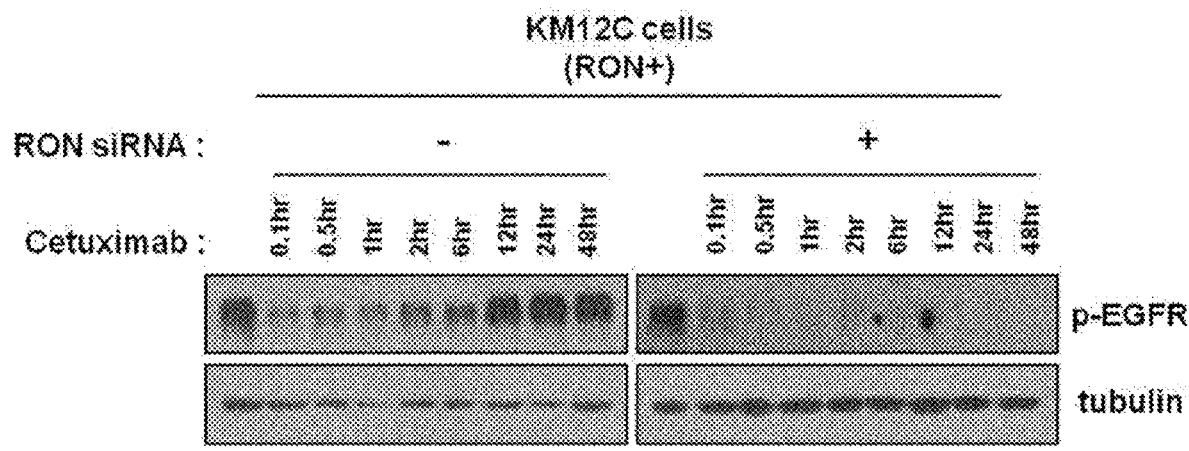
FIG. 5A illustrates an analysis result of inhibiting EGFR activation through inhibition of RON activation and inhibiting EGFR activation to cetuximab.

As a result, as illustrated in FIG. 5A, in the KM12C cell line without inhibiting the RON, even though cetuximab was treated, the activity of EGFR was reduced and then increased over the time, while in the KM12C cell line in which RON was inhibited with siRNA and cetuximab was treated, it was verified that the activity of the EGFR was rapidly reduced and then not increase, and therefore, it can be seen that the activity of the EGFR for cetuximab was regulated according to the presence of the RON.

5-2. Analysis of Cell Death of Cetuximab According to Presence of RON Activity

As listed in Table 6, it was known that the CaCo-2 colon cancer cell line had the KRAS, NRAS, and BRAF wild type genes and had susceptibility to cetuximab (Giovanni B. et al, Antitumoral Efficacy of the Protease Inhibitor Gabexate Mesilate in Colon Cancer Cells Harbouring KRAS, BRAF and PIK3CA Mutations. PLOS 2012, Volume 7, Issue 7, e41347).

TABLE 6

| Cell line | KRAS | BRAF |
|---|---|---|
| CACO-2* | wild-type | wild-type |
| SW48* | wild-type | wild-type |
| HT-29* | wild-type | mutation at exon 15 (V600E) |
| Colo205* | wild-type | mutation at exon 15 (V600E) |
| SW480** | mutation at exon 2 (G12V) | wild-type |

TABLE 6-continued

| Cell line | KRAS | BRAF |
| --- | --- | --- |
| SW620* | mutation at exon 2 (G12V) | wild-type |
| RKO* | wild-type | mutation at exon 15 (V600E) |
| LS174T* | mutation at exon 2 (G12V) | wild-type |
| HCT-116* | mutation at exon 2 (G12D) | wild-type |

Hereinabove, the inventors verified in Example 1-1 that the RON was not activated in the CaCo-2 colon cancer cell line.

Accordingly, in order to analyze the cell death degree according to the RON activity when cetuximab was treated, as described above, in order to verify the cetuximab reactivity in the CaCo-2 colon cancer cell line and the LIM1215 cell line which had KRAS, NRAS, and BRAF wild type genes and had susceptibility to cetuximab and in which the RON was not activated, and the KM12C colon cancer cell line in which the RON was activated and which had the resistance to cetuximab, the cell death was analyzed by trypan blue cell counting.

Figure 5B:
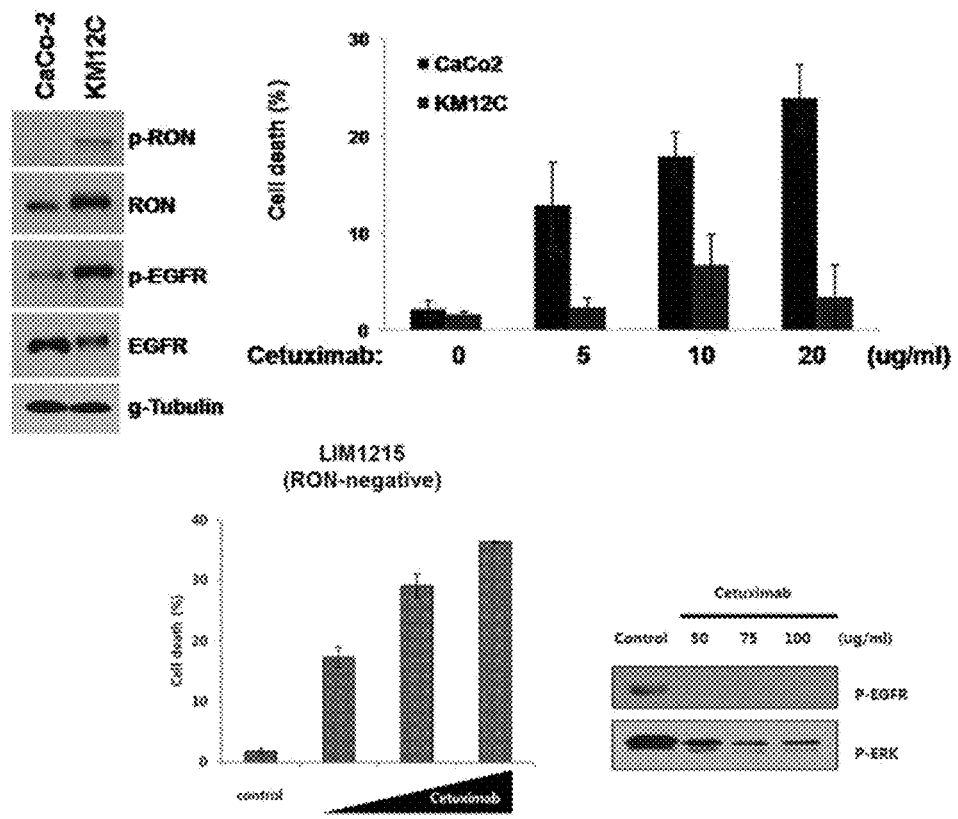
FIG. 5B illustrates an analysis result of cell death by cetuximab according to presence or absence of RON activation.

As a result, as illustrated in FIG. 5B, in the CaCo-2 cell line and the LIM1215 cell line in which the RON was not activated, the cell death by cetuximab was observed, while in the KM12C cell line in which the RON was activated, it can be seen that the cell death by cetuximab was not observed and the KM12C cell line had the resistance to cetuximab.

5-3. Analysis of Cell Death by Cetuximab after Inhibiting RON Expression

The inventors analyzed the cell death by trypan blue cell counting by treating cetuximab after artificially inhibiting the RON by the siRNA technique in the KM12C colon cancer cell line having the resistance to cetuximab in which the RON was activated.

Figure 5C:
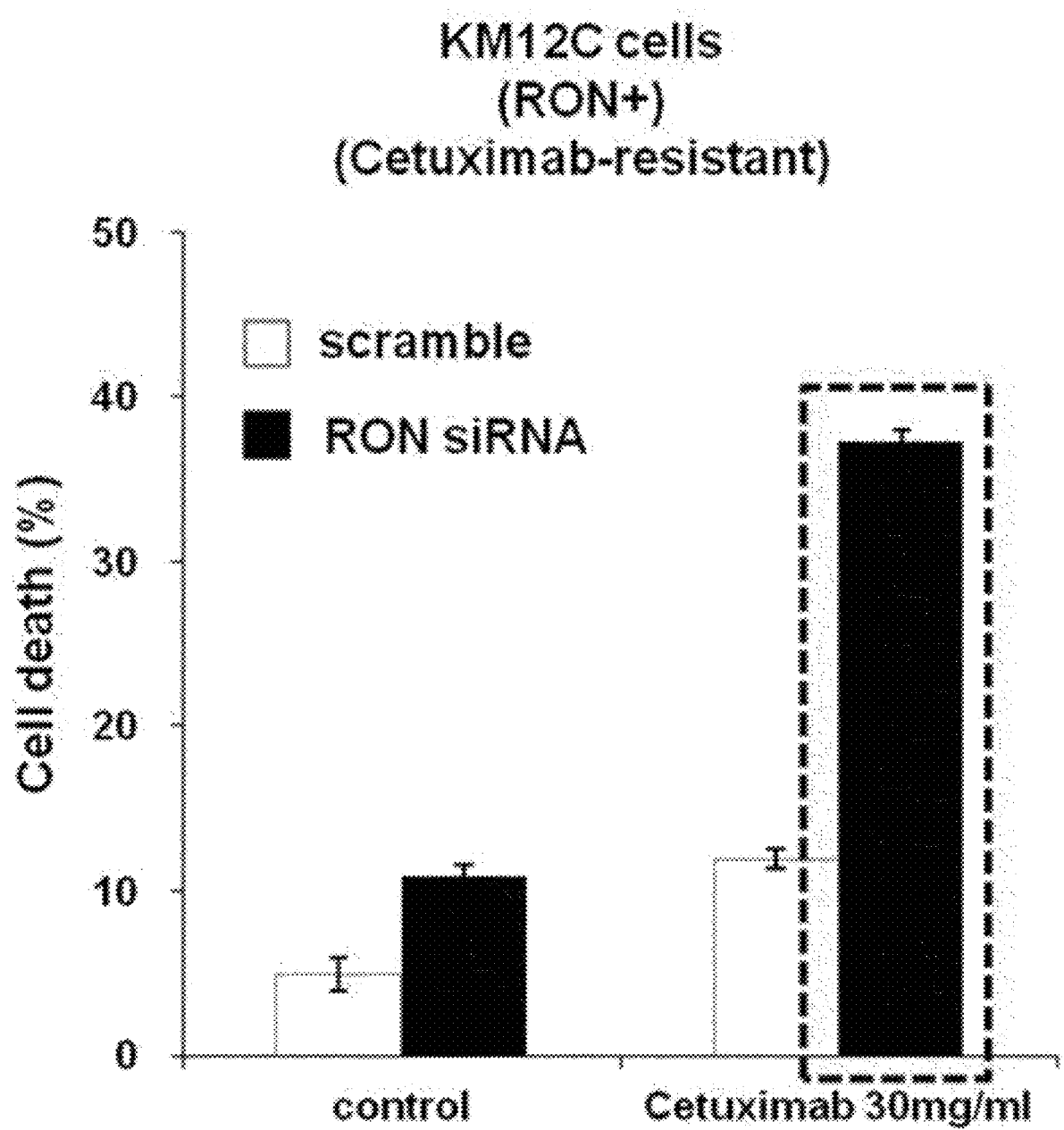
FIG. 5C illustrates an analysis result of cell death by cetuximab after inhibiting RON expression.

As a result, as illustrated in FIG. 5C, in the case of inhibiting the RON, it can be seen that the susceptibility to cetuximab was increased and the cell death was increased.

5-4. Analysis of Sub-Signaling Mechanism by Cetuximab after Inhibiting RON Expression The inventors observed a sub-signaling mechanism through western blot by treating cetuximab after artificially inhibiting the RON by the siRNA technique in the KM12C colon cancer cell line having the resistance to cetuximab in which the RON was activated.

Figure 5D:
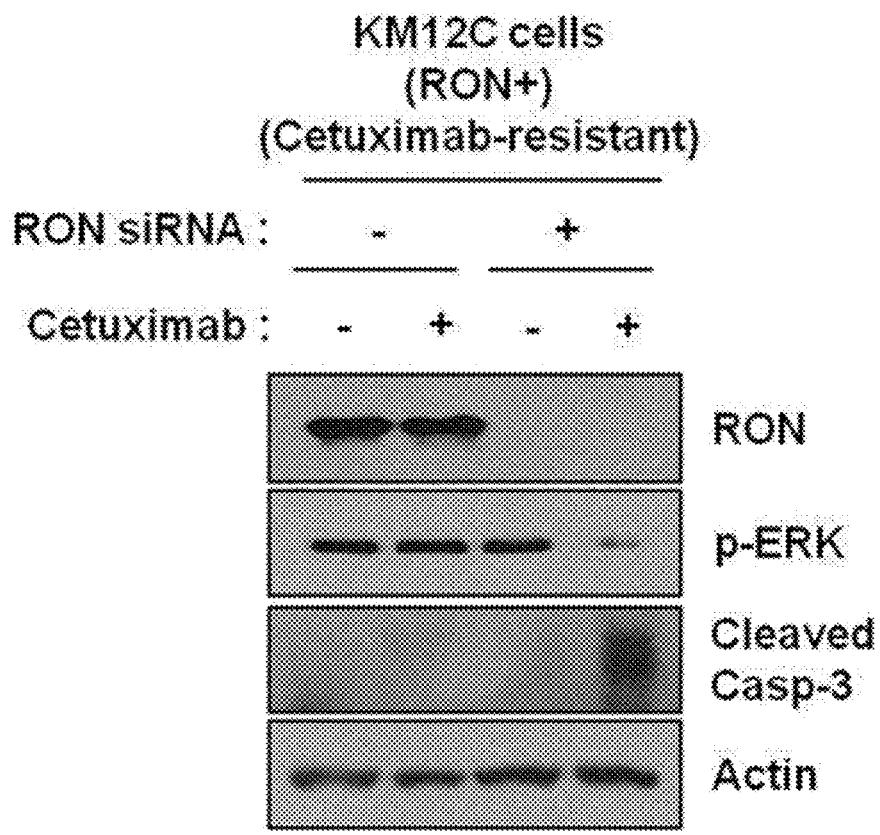
FIG. 5D illustrates an analysis result of a sub-signaling mechanism by cetuximab after inhibiting RON expression.

As a result, as illustrated in FIG. 5D, in the group in which the expression of the RON was inhibited and cetuximab was treated, it can be seen that a p-ERK protein that played an important role in cell survival was reduced and cleaved caspase-3 as an apoptosis marker protein was increased.

5-5. Analysis of Cell Death by Cetuximab after Inhibiting RON Activity

The inventors analyzed the cell death by trypan blue cell counting in the group in which an inhibitor LY2801653 capable of inhibiting the activity of the RON and cetuximab were treated, respectively, and the group in which the LY2801653 and cetuximab were treated together, in the KM12C colon cancer cell line having resistance to cetuximab in which the RON was activated.

Figure 5E:
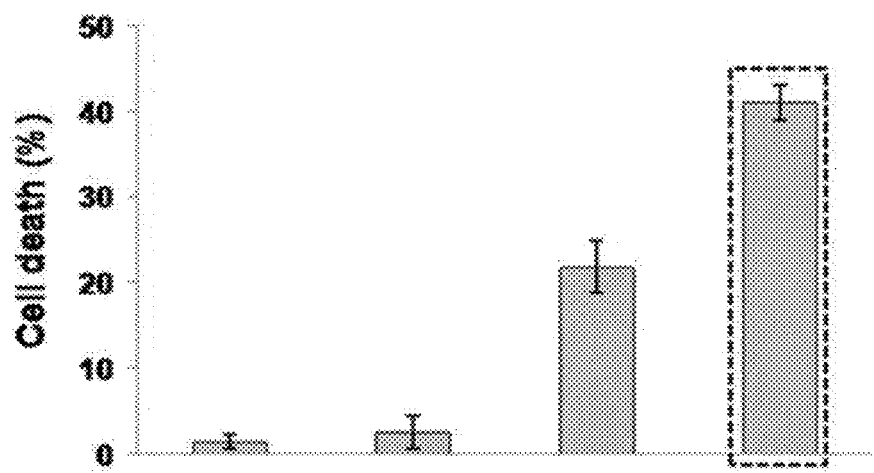
FIG. 5E illustrates an analysis result of cell death by cetuximab after inhibiting RON activation.

As a result, as illustrated in FIG. 5E, in the group in which the LY2801653, RON activity inhibitor and cetuximab were treated together, it can be seen that the cell death was increased.

5-6. Analysis of Cell Death by Cetuximab According to Activity of RON

The inventors observed the cell death for cetuximab after overexpressing Δ160 and Δ155 as the active forms of the RON in the CaCo-2 and SW48 colon cancer cell lines having the susceptibility to cetuximab in which the RON was not activated.

Figure 5F:
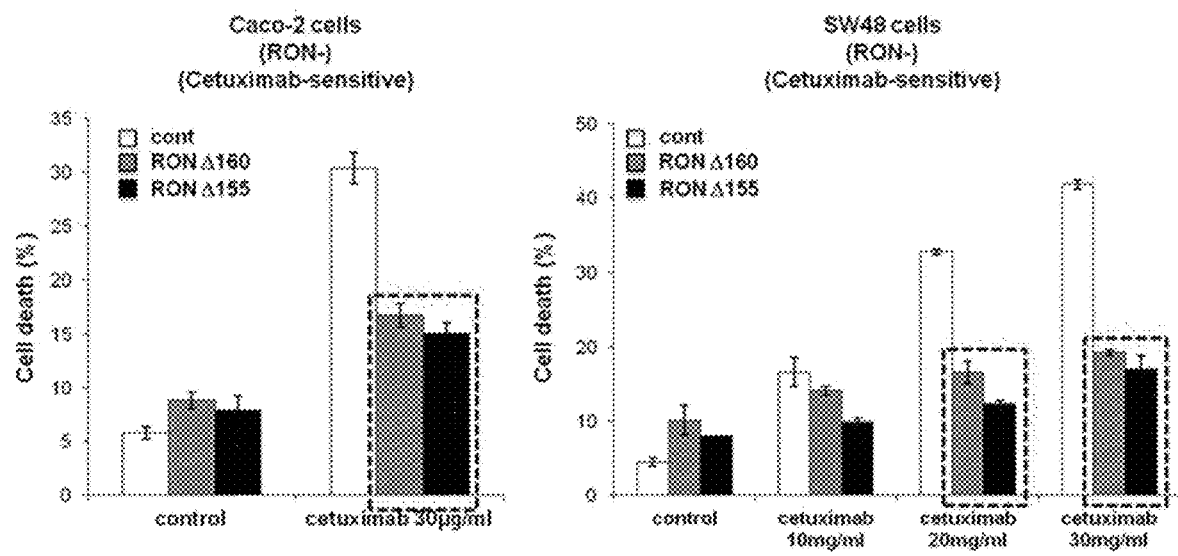
FIG. 5F illustrates an analysis result of cell death by cetuximab according to presence or absence of RON activation.

As a result, as illustrated in FIG. 5F, in the case of overexpressing the Δ160 and Δ155 as the active forms of the RON in the CaCo-2 and SW48 cell lines which had the susceptibility to cetuximab, it can be seen that the cell death was inhibited by cetuximab and the resistance to cetuximab was exhibited.

5-7. Analysis of Cell Growth Inhibition by Cetuximab According to Activity of RON The inventors observed the cell growth for cetuximab by a colony formation method by overexpressing the Δ160 variant as the active form of the RON in the CaCo-2 colon cancer cell line having the susceptibility to cetuximab in which the RON was not activated.

Figure 5G:
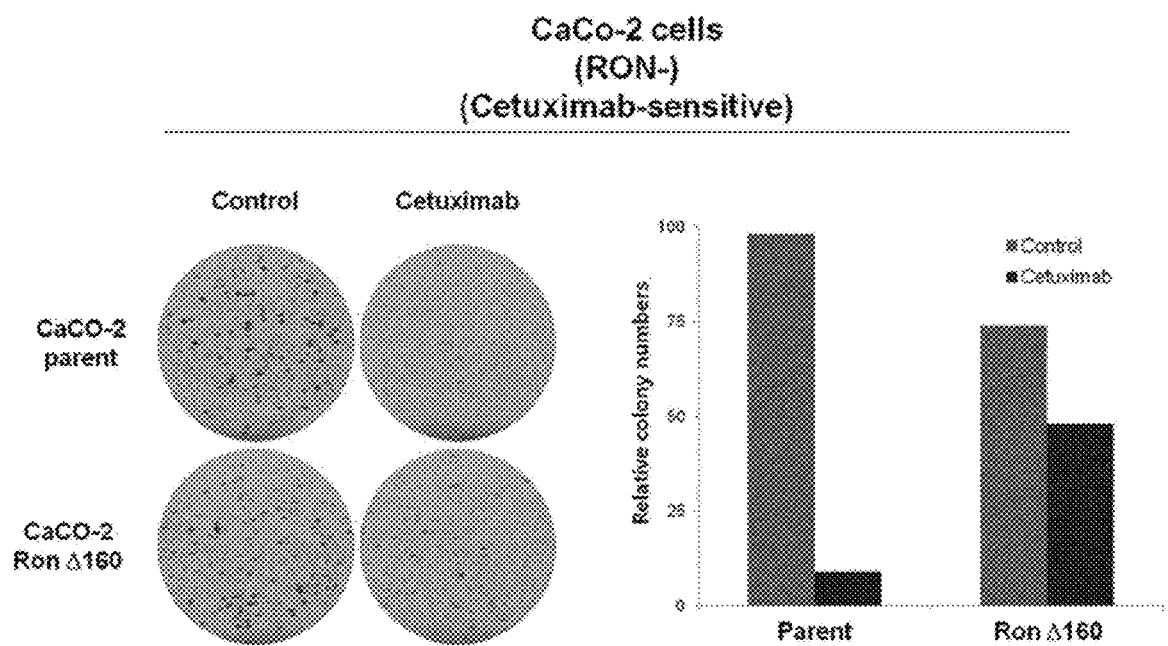
FIG. 5G illustrates an analysis result of inhibiting a cell growth by cetuximab according to presence or absence of RON activation.

As a result, as illustrated in FIG. 5G, in a parent CaCo-2 cell line of which the number of colonies was reduced by cetuximab, when the Δ160 variant as the active form of the RON was overexpressed, it can be seen that even though cetuximab was treated, the number of colonies was not almost reduced and the resistance of the cell growth to cetuximab was exhibited by the Δ160 protein as the active form of the RON.

5-8. Analysis of Cell Death by Cetuximab in RON Knockout Isogenic Cell Line

The inventors observed the cell death by treating cetuximab for each concentration in #1 clone with good RON knockout efficiency, in order to analyze the cell death and the cell growth for cetuximab by preparing a cell line in which the RON gene was knockout by using a CRISPR/Cas9 method in the KM12C colon cancer cell line having resistance to cetuximab in which the RON was activated.

Figure 5H:
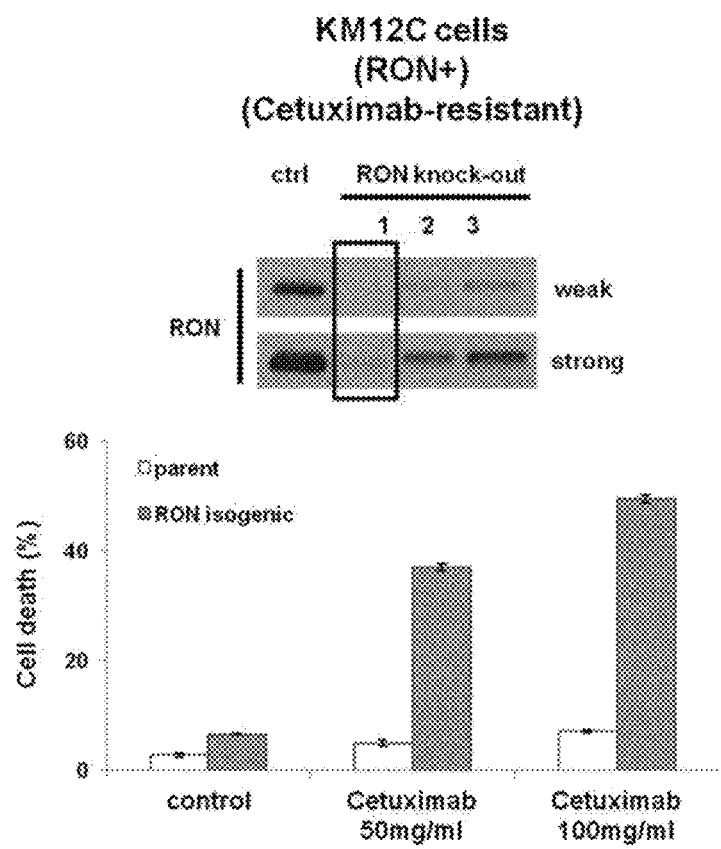
FIG. 5H illustrates an analysis result of cell death by cetuximab in a RON knockout isogenic cell line.

As a result, as illustrated in FIG. 5H, it was verified that the cell death was increased as compared with the parent cell line, and when knockoutting the RON, it can be seen that the susceptibility to cetuximab was increased.

5-9. Analysis of Cell Growth Inhibition by Cetuximab in RON Knockout Isogenic Cell Line The inventors observed the cell growth for cetuximab by a colony formation method by using a cell line in which the RON gene was knocked-out by using the CRISPR/Cas9 method in the KM12C colon cancer cell line having resistance to cetuximab in which the RON was activated.

Figure 5I:
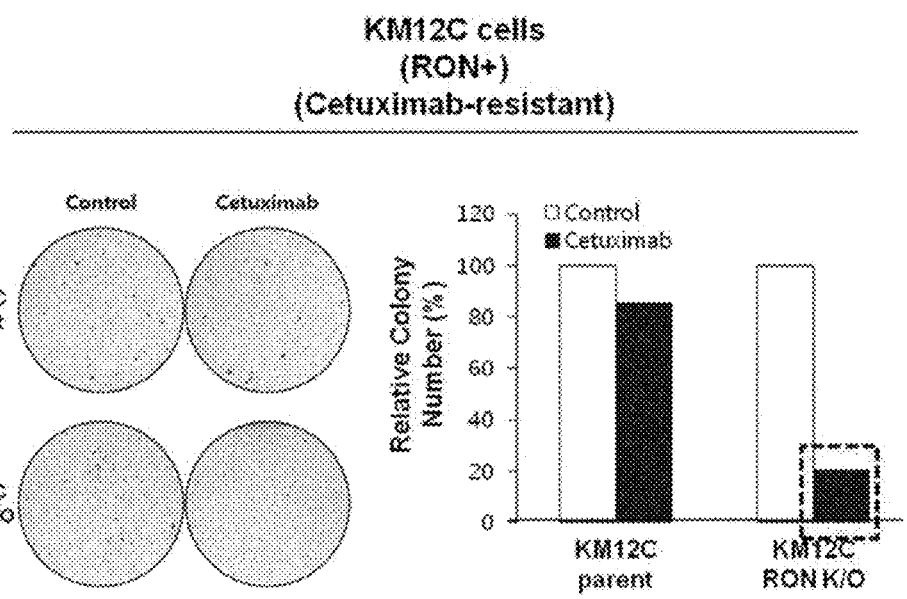
FIG. 5I illustrates an analysis result of cell growth inhibition by cetuximab in a RON knockout isogenic cell line.

As a result, as illustrated in FIG. 5I, it was verified that the number of colonies decreased as compared with the parent cell line, and when knockoutting the RON, it can be seen that the susceptibility to cetuximab was increased.

Example 6. Analysis of Tumor Inhibition Effect by Cetuximab According to RON in In Vivo Xenograft Model Using RON Knockout Isogenic Cell Line The inventors observed the tumor inhibition effect by cetuximab in an in vivo xenograft model by using a cell line in which the RON gene was knocked-out by using the CRISPR/Cas9 method in the KM12C colon cancer cell line having resistance to cetuximab in which the RON was activated.

Figure 6:
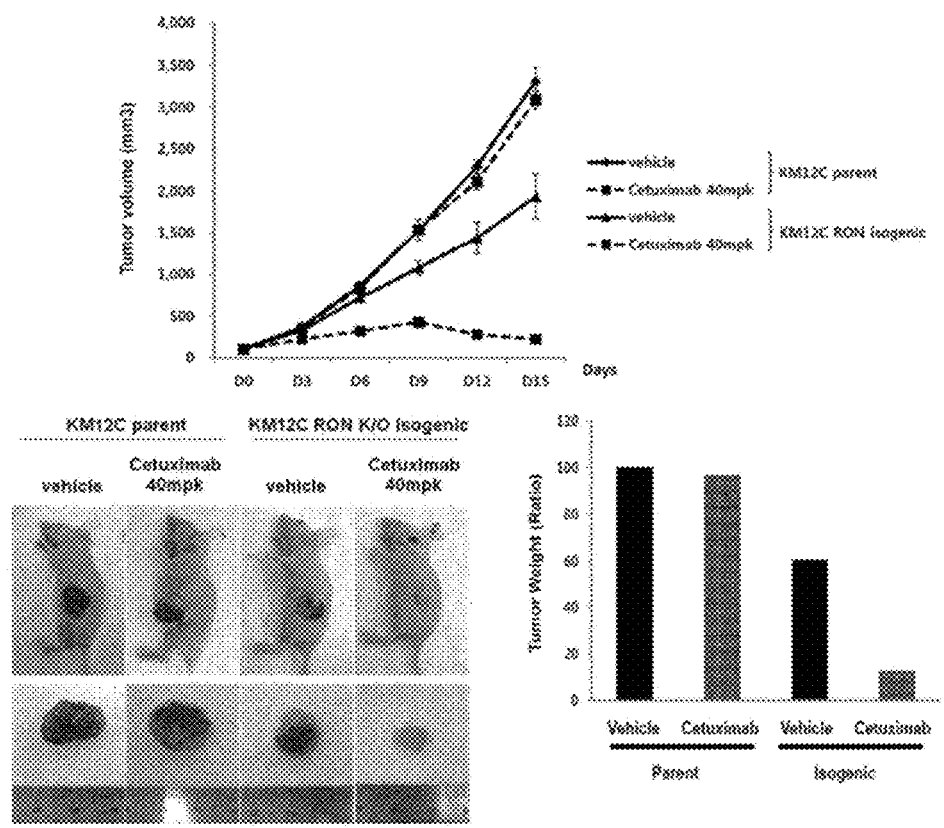
FIG. 6 illustrates an analysis result of a tumor inhibition effect of cetuximab according to presence or absence of RON in an in vivo xenograft model using a RON knockout isogenic cell line.

As a result, as illustrated in FIG. 6, as compared with the parent cell line, in the RON knockout xenograft mouse, it was observed that the size of the tumor was significantly reduced, and when the activation of the RON was knocked-out, it can be seen that the in vivo susceptibility by cetuximab was increased.

Accordingly, the activation of the RON exhibits possibility as the biomarker for predicting the susceptibility to cetuximab as the EGFR-targeted agent.

Example 7. Verification of Cell Death Induction by Treating RON Antibody Anticancer Agent and Cetuximab Together The inventors verified the cell death induction by treating an RON antibody anticancer agent and cetuximab together.

Figure 7:
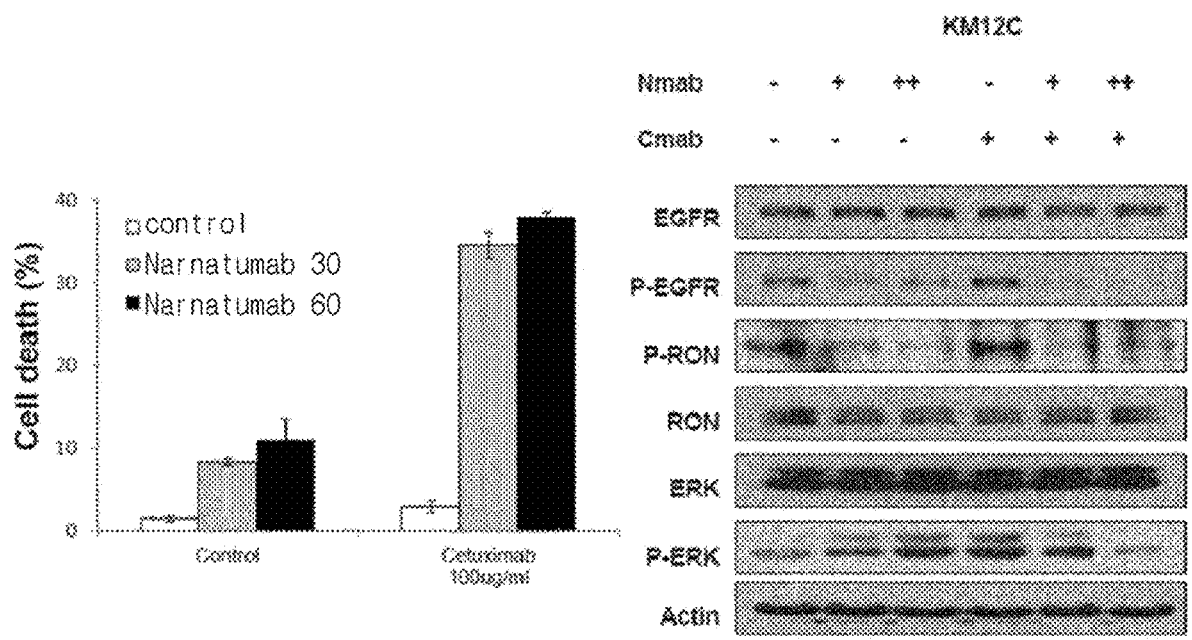
FIG. 7 illustrates a result of treating both an ROM antibody anticancer agent and cetuximab in a cell line having RON activation.

As a result, as illustrated in FIG. 7, when treating narnatumab and cetuximab which were antibody anticancer agents targeting the RON together, it was verified that the cell death was induced. In this case, when the change in expression of proteins was verified, it was verified that the activity of the EGFR and the RON was inhibited and the activity of the ERK was inhibited.

Example 8. Analysis Relationship Between Cetuximab Reactivity and RON Activity The inventors analyzed a relationship between cetuximab reactivity and RON activity.

Figure 8:
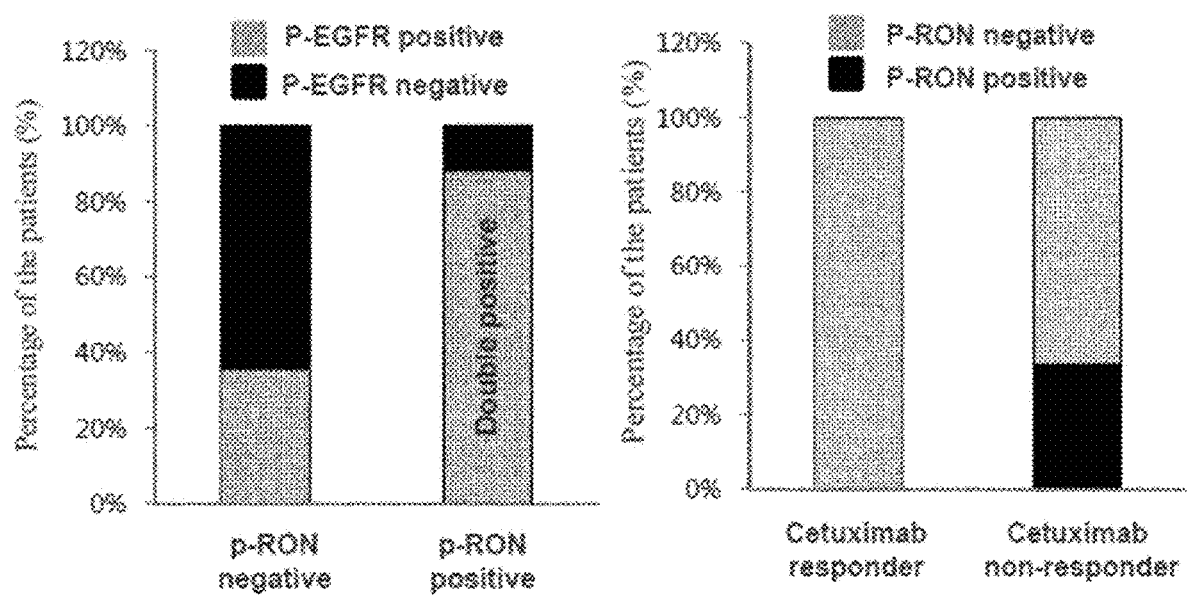
FIG. 8 illustrates a result of analyzing RON activation in tissue from colon cancer patient (treated with cetuximab).

As a result, as illustrated in FIG. 8, the colon cancer patients were verified as having RON active forms (p-RON positive) and EGFR active forms (P-EGFR positive) (see left graph). Further, it was verified that the patients prescribed with cetuximab among the colon cancer patients (double positive) had different susceptibility to cetuximab according to the RON activity.

What is claimed is:

1. A method for enhancing susceptibility to cetuximab, the method comprising:
   a. selecting a subject having colon cancer in which an expression level of RON (recepteur d'origine nantais) gene or an expression or activity level of a protein thereof in a biological sample from the subject is high as compared to a normal level; and
   b. administering a susceptibility enhancer to cetuximab and cetuximab to the subject having colon cancer, wherein the susceptibility enhancer comprises an inhibitor that inhibits an expression level of RON (recepteur d'origine nantais) gene; or an expression or activity level of a protein thereof as active ingredients, and wherein KRAS (V-Ki-ras2 Kirsten rate sarcoma viral oncogene homolog), NRAS (neuroblastoma RAS viral (v-ras) oncogene homolog), or BRAF (v-raf murine sarcoma viral oncogene homolog B) gene of the subject is a wild type.

2. The method of claim 1, wherein the inhibitor is one or more selected from the group consisting of small interference RNA (siRNA), short hairpin RNA (shRNA), microRNA (miRNA), ribozyme, DNAzyme, peptide nucleic acids (PNAs), antisense oligonucleotide, antibodies, aptamers, natural extracts, and chemical substances.

3. The method of claim 2, wherein the siRNA comprises a nucleotide sequence of SEQ ID NO:13.

* * * * *

SEQUENCE LISTING

<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
tggcttcctc ctctgtgtca a                                             21

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gcacttccct tcattgctgc                                               20

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
aatggcagat tggagggaaa tg                                            22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ttcatagcag gcaaatggag ca                                            22

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
tgactggctt gtgctatgtt gg                                            22

```
<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
atgcctgaag tgatgcccac                                                    20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggcagaatgg aagccaagga                                                    20

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
ttgctgttac gacgactggg tg                                                 22

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
atcgtgccct tcgccatcat                                                    20

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
ccagtcgtga ggtttcctaa gcag                                               24

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
agaaggctgg ggctcatttg                                                    20

<210> SEQ ID NO 12
<211> LENGTH: 20
<212> TYPE: DNA
<213> ORGANISM: Artificial Sequence
<220> FEATURE:
<223> OTHER INFORMATION: primer
```

```
<400> SEQUENCE: 12
aggggccatc cacagtcttc                                           20

<210> SEQ ID NO 13
<211> LENGTH: 21
<212> TYPE: RNA
<213> ORGANISM: Artificial Sequence
<220> FEATURE:
<223> OTHER INFORMATION: siRNA

<400> SEQUENCE: 13 acuuguaga ggaguuugau u                                          21
```